US009764124B2

(12) United States Patent
Tallarida et al.

(10) Patent No.: US 9,764,124 B2
(45) Date of Patent: Sep. 19, 2017

(54) VASCULAR ACCESS PORT

(71) Applicant: STD Med, Inc., Stoughton, MA (US)

(72) Inventors: Steven J. Tallarida, Mansfield, MA (US); Richard P. Rodgers, Hudson, MA (US); John M. Butziger, East Greenwich, RI (US)

(73) Assignee: Versago Vascular Access, Inc., West Bridgewater, MA (US)

( * ) Notice: Subject to any disclaimer, the term of this patent is extended or adjusted under 35 U.S.C. 154(b) by 0 days.

(21) Appl. No.: 14/231,392

(22) Filed: Mar. 31, 2014

(65) Prior Publication Data

US 2015/0273201 A1 Oct. 1, 2015

(51) Int. Cl.
*A61M 39/02* (2006.01)
*A61M 39/22* (2006.01)

(52) U.S. Cl.
CPC ........ *A61M 39/0208* (2013.01); *A61M 39/22* (2013.01); *A61M 2039/0226* (2013.01);
(Continued)

(58) Field of Classification Search
CPC ........ A61M 39/0208; A61M 2039/022; A61M 2205/0272; A61M 2039/0226; A61M 2039/0235; A61M 31/00; A61M 2039/02967; A61M 2039/0202; A61M 2039/0205; A61M 2039/0211–2039/0244; A61M 39/22; A61M 2205/04
See application file for complete search history.

(56) References Cited

U.S. PATENT DOCUMENTS

| 3,819,282 A | 6/1974 | Schultz |
|---|---|---|
| 4,181,132 A | 1/1980 | Parks |

(Continued)

FOREIGN PATENT DOCUMENTS

| WO | 9701370 | 1/1997 |
|---|---|---|
| WO | 2016/100868 | 6/2016 |
| WO | 2016/100945 | 6/2016 |

OTHER PUBLICATIONS

Remove Definition, Merriam-Webster Inc, 2015.*
(Continued)

*Primary Examiner* — Bradley Osinski
(74) *Attorney, Agent, or Firm* — Grossman Tucker Perreault & Pfleger PLLC

(57) ABSTRACT

An implantable vascular access port for providing repeated therapy to a patient in need of such therapy, the access port, upon repeated use, presents each time an access needle at a new location so as to minimize scarring injury to the skin of the patient. The vascular access port may include a body, a cover comprising a plurality of openings, at least one needle comprising a tip and a shaft, the shaft defining a lumen, a needle elevator mechanism to operate the position of the at least one needle in at least a retracted position in which the at least one needle is disposed in the body and the needle tip below the cover and an extended position in which the at least one needle is engaged through at least a first one of the openings, and a needle shift mechanism to move the at least one needle from a first position in which the needle can engage the at least a first one of the openings, to a second position in which the needle can engage at least a second one of the openings.

21 Claims, 24 Drawing Sheets

(52) U.S. Cl.
CPC ............. *A61M 2039/0235* (2013.01); *A61M 2205/0272* (2013.01); *A61M 2205/04* (2013.01)

(56) References Cited

U.S. PATENT DOCUMENTS

| | | |
|---|---|---|
| 4,190,040 A | 2/1980 | Schulte |
| 4,228,802 A | 10/1980 | Trott |
| 4,445,896 A | 5/1984 | Gianturco |
| 4,543,088 A | 9/1985 | Bootman et al. |
| 4,576,595 A | 3/1986 | Aas et al. |
| 4,673,394 A | 6/1987 | Fenton, Jr. et al. |
| 4,692,146 A | 9/1987 | Hilger |
| 4,710,167 A | 12/1987 | Lazorthes |
| 4,760,837 A | 8/1988 | Petit |
| 4,781,680 A | 11/1988 | Redmond et al. |
| 4,802,885 A | 2/1989 | Weeks et al. |
| 4,840,615 A | 6/1989 | Hancock et al. |
| 4,892,518 A | 1/1990 | Cupp et al. |
| 4,904,241 A | 2/1990 | Bark |
| 4,919,653 A | 4/1990 | Martinez et al. |
| 4,929,236 A | 5/1990 | Sampson |
| 5,006,115 A | 4/1991 | McDonald |
| 5,041,098 A | 8/1991 | Loiterman et al. |
| 5,084,015 A | 1/1992 | Moriuchi |
| 5,137,529 A | 8/1992 | Watson et al. |
| 5,203,771 A | 4/1993 | Melker et al. |
| 5,213,574 A | 5/1993 | Tucker |
| 5,215,530 A | 6/1993 | Hogan |
| 5,234,406 A | 8/1993 | Drasner et al. |
| 5,281,199 A | 1/1994 | Ensminger et al. |
| 5,295,658 A | 3/1994 | Atkinson et al. |
| 5,306,255 A | 4/1994 | Haindl |
| 5,318,545 A | 6/1994 | Tucker |
| 5,332,398 A | 7/1994 | Miller et al. |
| 5,337,756 A | 8/1994 | Barbier et al. |
| 5,338,398 A | 8/1994 | Szwejkowski et al. |
| 5,350,360 A | 9/1994 | Ensminger et al. |
| 5,352,204 A | 10/1994 | Ensminger |
| 5,360,407 A | 11/1994 | Leonard |
| 5,387,192 A | 2/1995 | Glantz et al. |
| 5,391,801 A | 2/1995 | Sato et al. |
| 5,399,168 A | 3/1995 | Wadsworth, Jr. et al. |
| 5,417,656 A | 5/1995 | Ensminger et al. |
| 5,476,460 A | 12/1995 | Montalvo |
| 5,520,643 A | 5/1996 | Ensminger et al. |
| 5,527,278 A | 6/1996 | Ensminger et al. |
| 5,556,381 A | 9/1996 | Ensminger et al. |
| 5,558,641 A | 9/1996 | Glantz et al. |
| 5,562,617 A | 10/1996 | Finch, Jr. et al. |
| 5,562,618 A | 10/1996 | Cai et al. |
| 5,613,945 A | 3/1997 | Cai et al. |
| 5,637,088 A | 6/1997 | Wenner et al. |
| 5,647,855 A | 7/1997 | Trooskin |
| 5,695,490 A | 12/1997 | Flaherty et al. |
| 5,702,413 A | 12/1997 | Lafontaine |
| 5,704,915 A | 1/1998 | Melsky et al. |
| 5,718,682 A | 2/1998 | Tucker |
| 5,718,692 A | 2/1998 | Schon et al. |
| 5,792,104 A | 8/1998 | Speckman et al. |
| 5,792,123 A | 8/1998 | Ensminger |
| 5,797,879 A | 8/1998 | DeCampli |
| 5,833,654 A | 11/1998 | Powers et al. |
| 5,836,935 A | 11/1998 | Ashton et al. |
| 5,843,069 A | 12/1998 | Butler et al. |
| 5,848,989 A | 12/1998 | Villani |
| 5,931,801 A | 8/1999 | Burbank et al. |
| 5,951,512 A | 9/1999 | Dalton |
| 5,954,691 A | 9/1999 | Prosl |
| 5,989,206 A | 11/1999 | Prosl et al. |
| 6,007,516 A | 12/1999 | Burbank et al. |
| 6,030,397 A | 2/2000 | Monetti et al. |
| 6,039,712 A | 3/2000 | Fogarty et al. |
| 6,113,572 A | 9/2000 | Gailey et al. |
| 6,190,352 B1 | 2/2001 | Haarala et al. |
| 6,213,973 B1 | 4/2001 | Eliasen et al. |
| 6,478,783 B1 | 11/2002 | Moorehead |
| 6,527,754 B1 | 3/2003 | Tallarida et al. |
| 6,962,577 B2 | 11/2005 | Tallarida et al. |
| 6,981,977 B2 | 1/2006 | Herweck et al. |
| 7,056,316 B1 | 6/2006 | Burbank et al. |
| 7,131,962 B1 | 11/2006 | Estabrook et al. |
| 7,351,233 B2 | 4/2008 | Parks |
| 7,452,354 B2 | 11/2008 | Bright et al. |
| 7,713,251 B2 | 5/2010 | Tallarida et al. |
| 7,803,143 B2 | 9/2010 | Tallarida et al. |
| 7,811,266 B2 | 10/2010 | Eliasen |
| 8,182,453 B2 | 5/2012 | Eliasen |
| 8,409,153 B2 | 4/2013 | Tallarida et al. |
| 8,529,525 B2 | 9/2013 | Gerber et al. |
| 2001/0016713 A1 | 8/2001 | Takagi et al. |
| 2002/0095122 A1 | 7/2002 | Shaffer |
| 2003/0109837 A1 | 6/2003 | McBride-Sakal |
| 2004/0097930 A1 | 5/2004 | Justis et al. |
| 2004/0158207 A1 | 8/2004 | Hunn et al. |
| 2005/0014993 A1 | 1/2005 | Mische |
| 2005/0209619 A1* | 9/2005 | Johnson et al. ............... 606/167 |
| 2006/0004325 A1 | 1/2006 | Hamatake et al. |
| 2006/0178648 A1 | 8/2006 | Barron et al. |
| 2006/0224129 A1 | 10/2006 | Beasley et al. |
| 2007/0078432 A1 | 4/2007 | Halseth et al. |
| 2007/0233019 A1* | 10/2007 | Forsell ..................... 604/288.03 |
| 2007/0265595 A1 | 11/2007 | Miyamoto et al. |
| 2008/0039820 A1* | 2/2008 | Sommers et al. ............ 604/539 |
| 2008/0243106 A1 | 10/2008 | Coe et al. |
| 2008/0262475 A1 | 10/2008 | Preinitz |
| 2011/0137288 A1* | 6/2011 | Tallarida et al. .............. 604/513 |
| 2012/0209180 A1 | 8/2012 | Gray et al. |
| 2012/0232501 A1 | 9/2012 | Eliasen |
| 2013/0218103 A1 | 8/2013 | Tallarida et al. |
| 2013/0226101 A1 | 8/2013 | Westcott |
| 2013/0231637 A1 | 9/2013 | Tallarida et al. |
| 2015/0273201 A1 | 10/2015 | Tallarida et al. |
| 2016/0175560 A1 | 6/2016 | Tallarida et al. |
| 2016/0175575 A1 | 6/2016 | Tallarida et al. |
| 2017/0000995 A1 | 1/2017 | Tallarida et al. |
| 2017/0014611 A1 | 1/2017 | Butziger et al. |

OTHER PUBLICATIONS

U.S. Office Action dated Jan. 15, 2016, issued in U.S. Appl. No. 13/770,732, 23 pages.
International Search Report and Written Opinion dated Feb. 26, 2016, issued in PCT Patent Application Serial No. PCT/US2015/066934, 11 pages.
U.S. Office Action dated Dec. 2, 2014, issued in U.S. Appl. No. 13/770,732, 15 pages.
U.S. Office Action dated Jun. 10, 2015, issued in U.S. Appl. No. 13/770,732, 14 pages.
International Search Report and Written Opinion dated Jul. 2, 2015, issued in PCT Patent Application No. PCT/US2015/023590, 11 pages.
International Search Report and Written Opinion dated Jul. 10, 2015, issued in PCT Patent Application No. PCT/US2015/024256, 10 pages.
International Search Report and Written Opinion dated Mar. 7, 2016, issued in PCT Patent Application Serial No. PCT/US2015/066778, 9 pages.
Notice of Allowance dated Jun. 15, 2016, issued in U.S. Appl. No. 13/170,732, 9 pages.
Corrected Notice of Allowability dated Jul. 12, 2016, issued in U.S. Appl. No. 13/770,732, 6 pages.
Corrected Notice of Allowability dated Aug. 2, 2016, issued in U.S. Appl. No. 13/770,732, 6 pages.
PCT International Search Report dated Nov. 21, 2001 issued in PCT Application No. PCT/US01/13749, 4 pages.
PCT Written Opinion dated Dec. 19, 2002 issued in PCT Application PCT/US01/13749, 5 pages.
PCT Preliminary Examination Report dated May 28, 2003 issued in PCT Application PCT/US01/13749, 2 pages.

(56) References Cited

OTHER PUBLICATIONS

European Examination Report dated Jul. 30, 2003 issued in European Patent Application No. 99 964 086.5, 5 pages.
U.S. Office Action dated Aug. 27, 2003 issued in U.S. Appl. No. 09/842,458, 8 pages.
U.S. Office Action dated Dec. 23, 2003 issued in U.S. Appl. No. 09/842,458, 7 pages.
European Examination Report dated Mar. 9, 2004 issued in European Patent Application No. 99 964 086.5, 4 pages.
U.S. Notice of Allowance dated Oct. 15, 2004 issued in U.S. Appl. No. 09/842,458, 7 pages.
Australian Examination Report dated Jan. 21, 2005 issued in Australian Patent Application No. 2001257388, 2 pages.
U.S. Notice of Allowance dated Feb. 24, 2005 issued in U.S. Appl. No. 09/842,458, 6 pages.
European Examination Report dated Mar. 1, 2005 issued in European Patent Application No. 99 964 086.5, 4 pages.
European Examination Report dated Mar. 30, 2005 issued in European Patent Application No. 99 964 086.5, 3 pages.
European Decision to Refuse dated Dec. 15, 2005 issued in European Patent Application No. 99 964 086.5, 9 pages.
U.S. Office Action dated Feb. 14, 2007 issued in U.S. Appl. No. 10/890,909, 12 pages.
U.S. Office Action dated Apr. 11, 2007 issued in U.S. U.S. Appl. No. 10/931,890, 7 pages.
U.S. Office Action dated Sep. 13, 2007 issued in U.S. Appl. No. 10/890,909, 11 pages.
U.S. Office Action dated Sep. 13, 2007 issued in U.S. Appl. No. 10/931,890, 7 pages.
Canadian Office Action dated Oct. 16, 2007 issued in Canadian Patent Application No. 2,407,643, 2 pages.
U.S. Office Action dated Feb. 21, 2008 issued in U.S. Appl. No. 11/269,098, 19 pages.
U.S. Office Action dated Jun. 9, 2008 issued in U.S. Appl. No. 10/931,890, 10 pages.
U.S. Office Action dated Oct. 30, 2008 issued in U.S. Appl. No. 11/269,098, 12 pages.
U.S. Office Action dated Dec. 23, 2008 issued in U.S. Appl. No. 10/931,890, 9 pages.
U.S. Office Action dated Jun. 4, 2009 issued in U.S. Appl. No. 11/269,098, 11 pages.
Supplemental European Search Report dated Jun. 10, 2009 issued in European Patent Application No. 01 930 898.0, 4 pages.
U.S. Office Action dated Aug. 3, 2009 issued in U.S. Appl. No. 10/931,890, 10 pages.
European Examination Report dated Oct. 2, 2009 issued in European Patent Application No. 01 930 898.0, 4 pages.
U.S. Office Action dated Mar. 3, 2010 issued in U.S. Appl. No. 11/269,098, 15 pages.
U.S. Office Action dated Feb. 17, 2011 issued in U.S. Appl. No. 12/902,839, 17 pages.
U.S. Office Action dated Oct. 17, 2011 issued in U.S. Appl. No. 12/902,839, 11 pages.
Notice of Allowance dated Feb. 1, 2012 issued in U.S. Appl. No. 12/902,839, 7 pages.
European Office Action dated Oct. 23, 2012 issued in European Patent Application No. 01 930 898.0, 4 pages.
U.S. Office Action dated Feb. 28, 2007 issued in U.S. Appl. No. 10/374,000, 8 pages.
U.S. Office Action dated Aug. 28, 2007 issued in U.S. Appl. No. 10/374,000, 8 pages.
U.S. Office Action dated Mar. 20, 2008 issued in U.S. Appl. No. 10/374,000, 7 pages.
U.S. Office Action dated Sep. 30, 2008 issued in U.S. Appl. No. 10/374,000, 8 pages.
U.S. Office Action dated May 20, 2009 issued in U.S. Appl. No. 10/374,000, 10 pages.
Access technologies, The V-A-Pu . . . Vascular Access and Beyond, downloaded from internet Jul. 28, 2009, http://www.norfolkaccess.com/VAPs.html, 4 pages.
SyncMedical, Innovative Surgical Devices, Primo Port Products, downloaded from internet Jul. 28, 2009, http://www.syncmedical.com/primo-port, 2 pages.
U.S. Office Action dated Oct. 23, 2014 issued in U.S. Appl. No. 13/477,997, 14 pages.
International Preliminary Report on Patentability dated Oct. 13, 2016, issued in PCT International Patent Application No. PCT/US2015/024256, 8 pages.
International Search Report and Written Opinion dated Oct. 7, 2016, issued in PCT International Patent Application No. PCT/US2016/042272, 11 pages.
International Preliminary Report on Patentability dated Oct. 13, 2016, issued in PCT International Patent Application No. PCT/US2015/023590, 9 pages.

\* cited by examiner

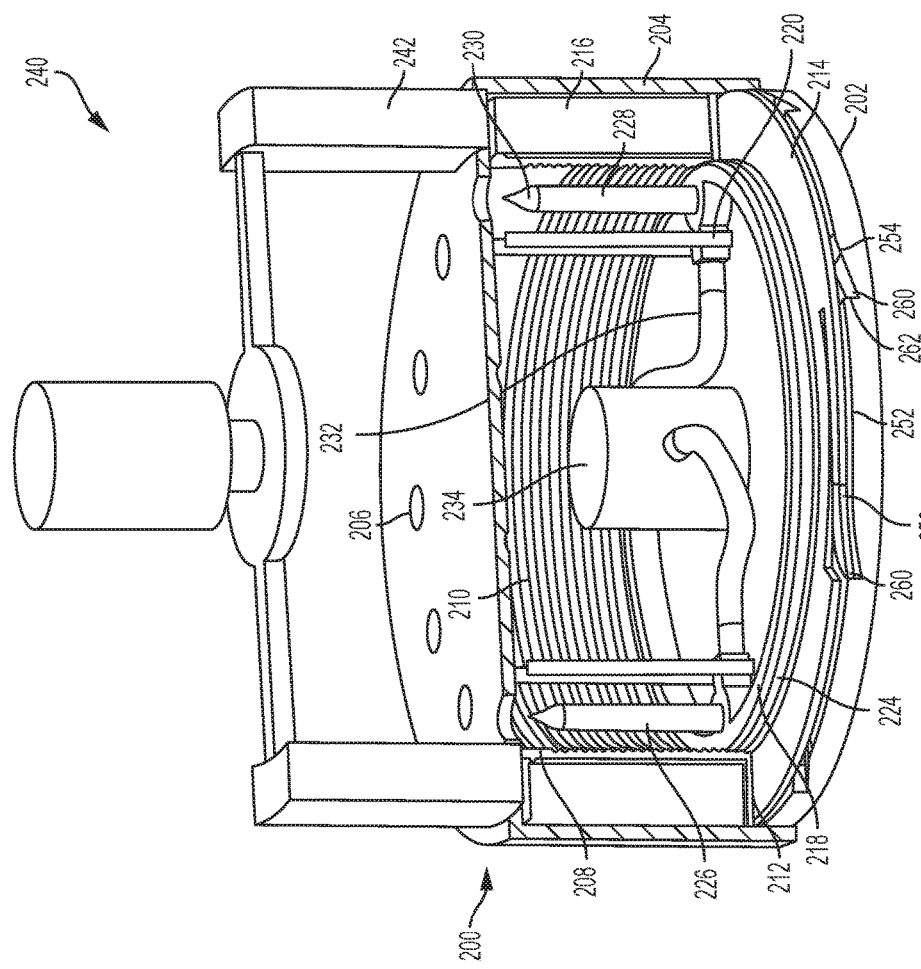

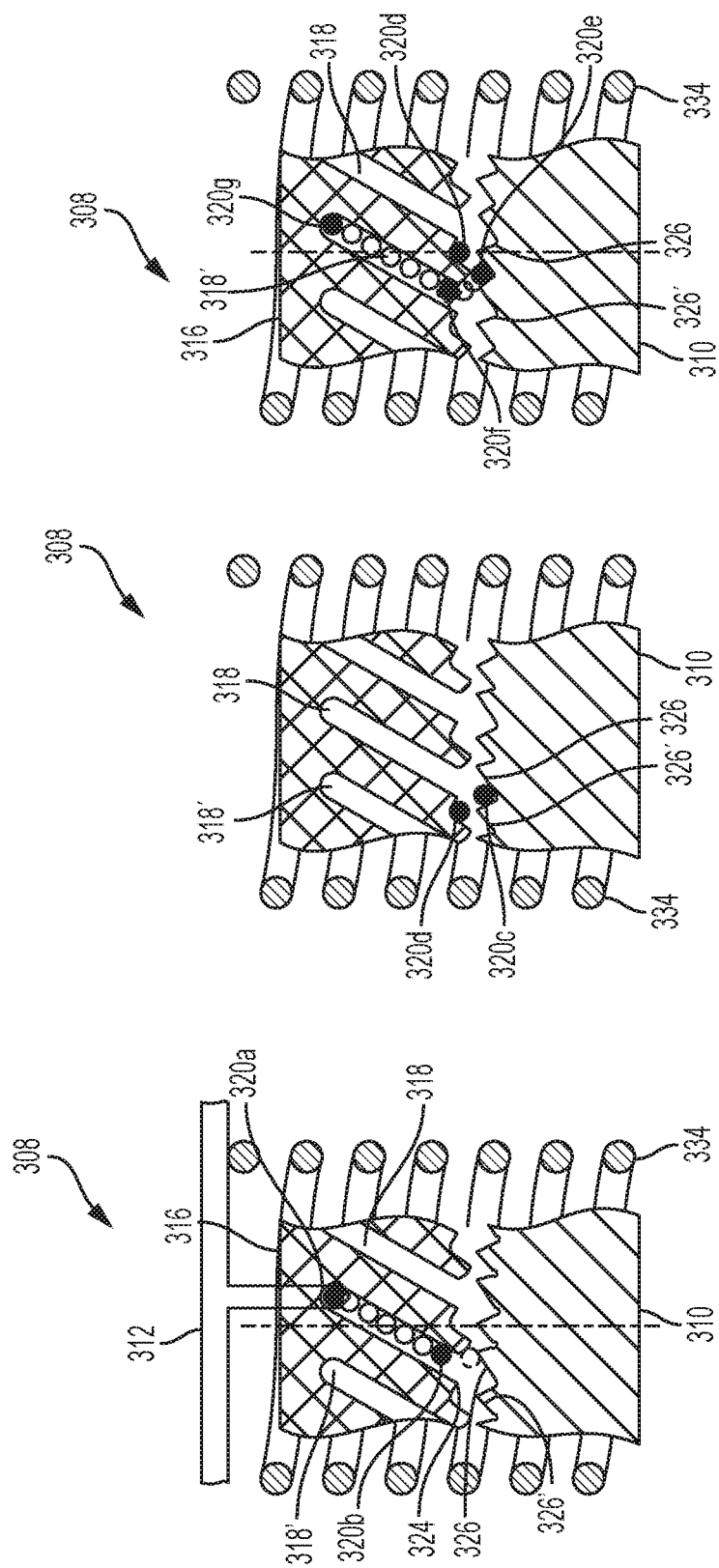

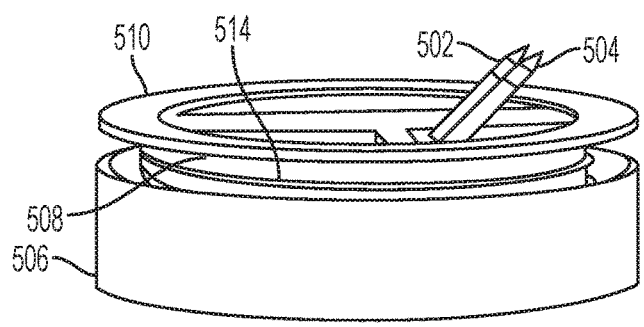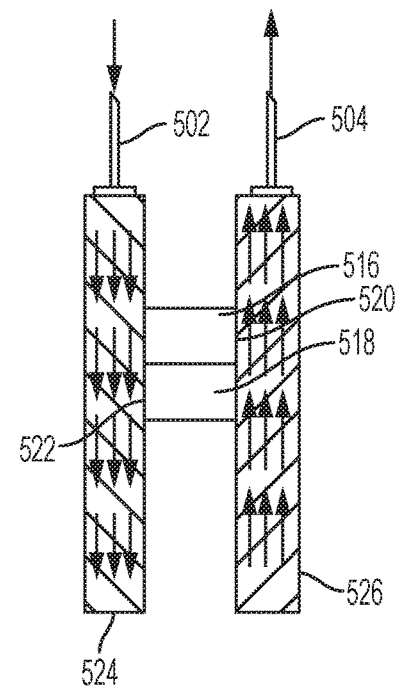
FIG. 5a
FIG. 5b
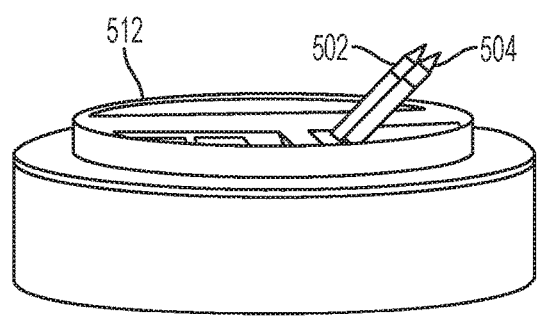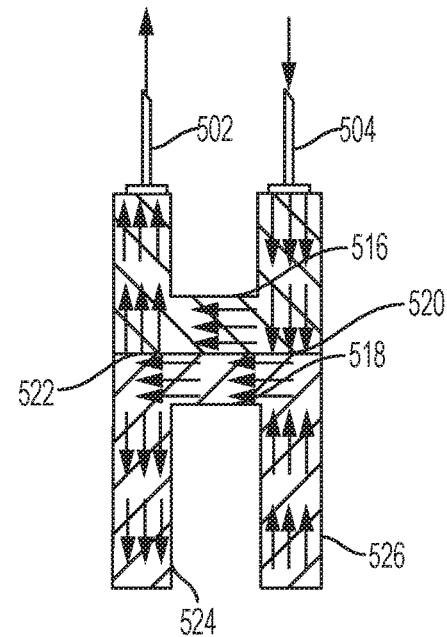
FIG. 5c
FIG. 5d

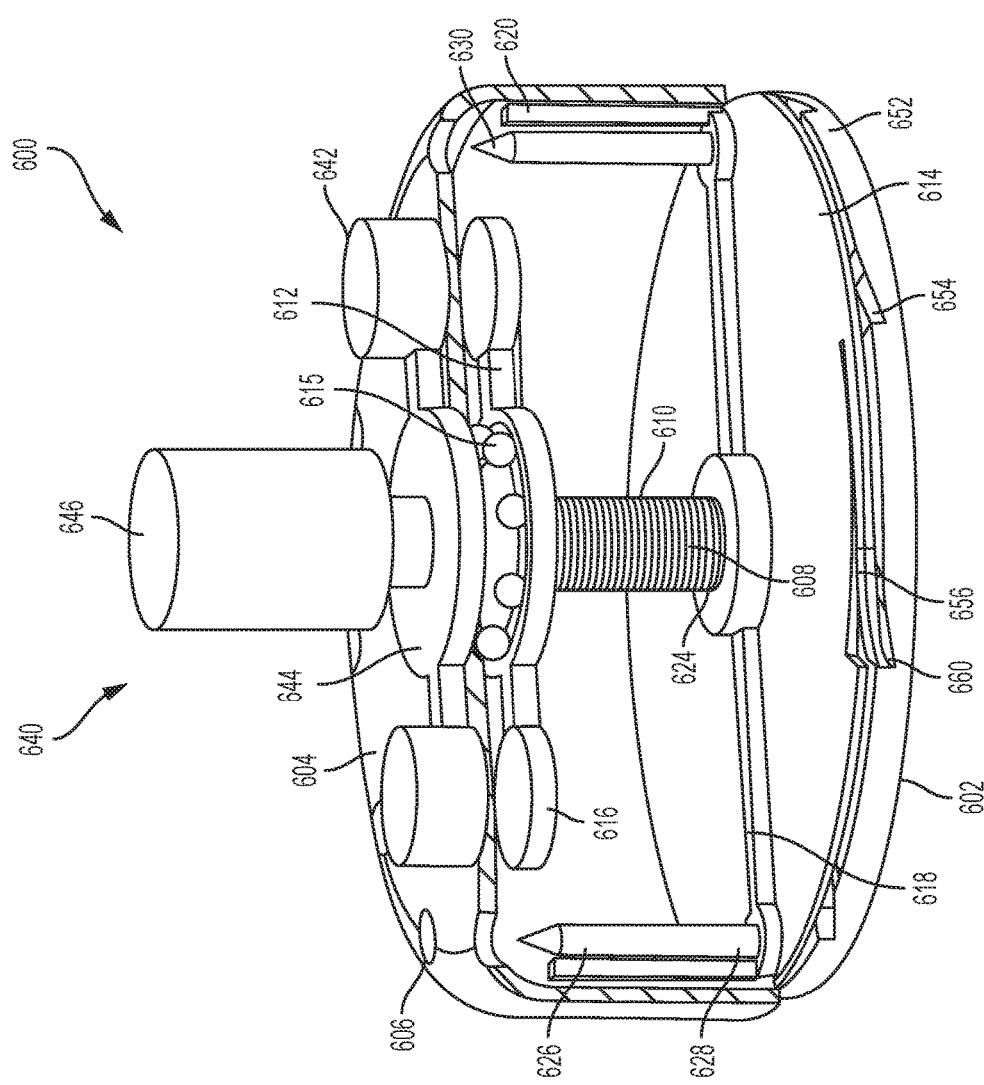

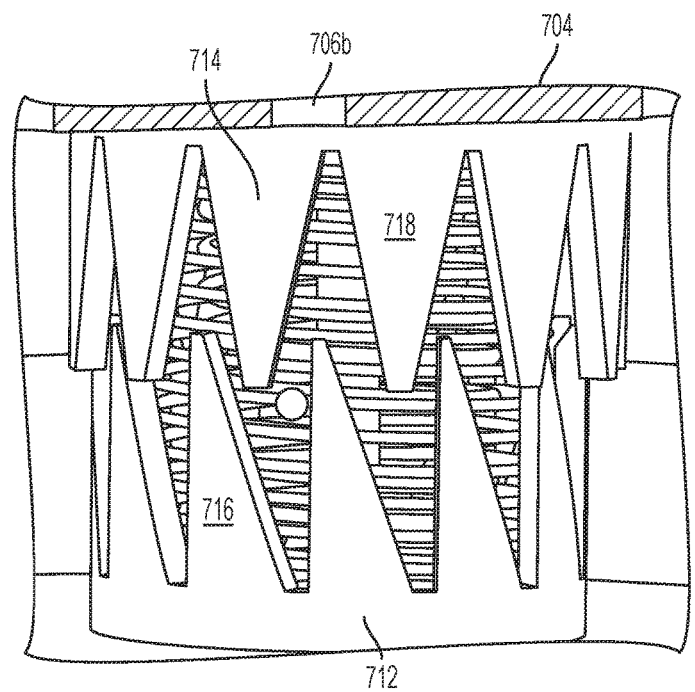
FIG. 8a
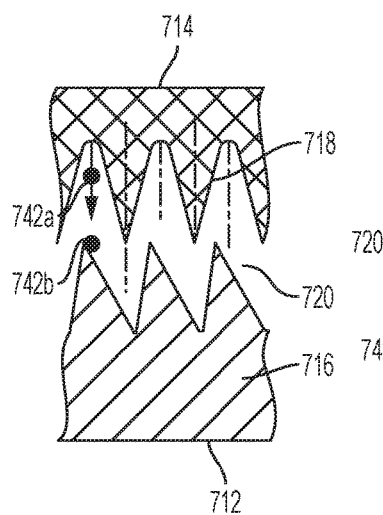 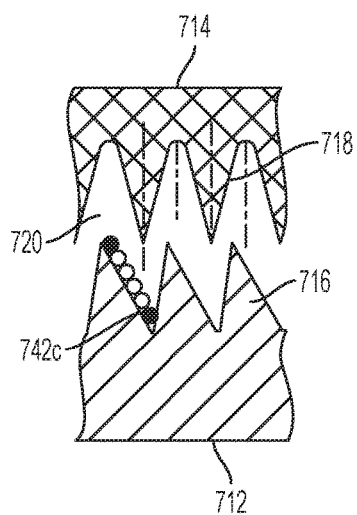 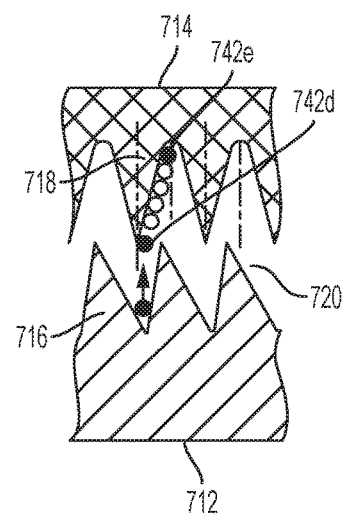
FIG. 8b  FIG. 8c  FIG. 8d

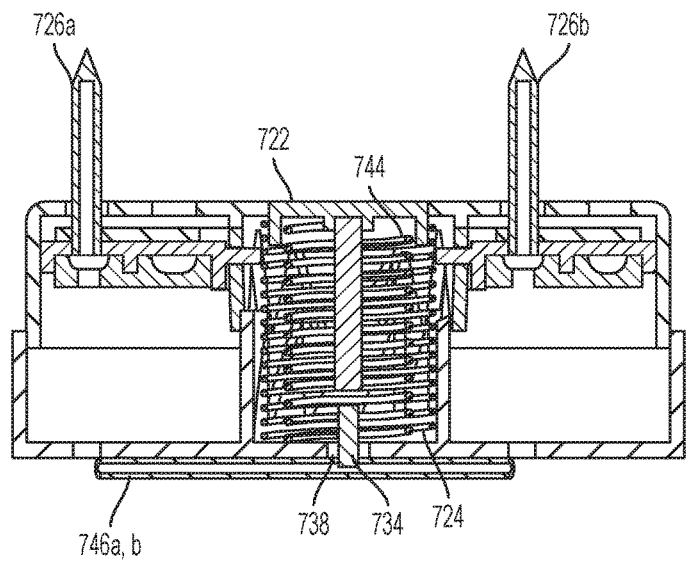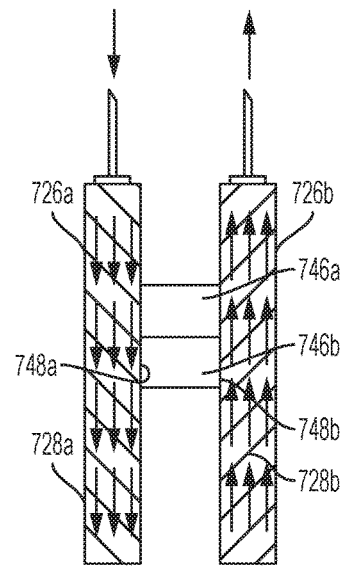
FIG. 9a    FIG. 9b
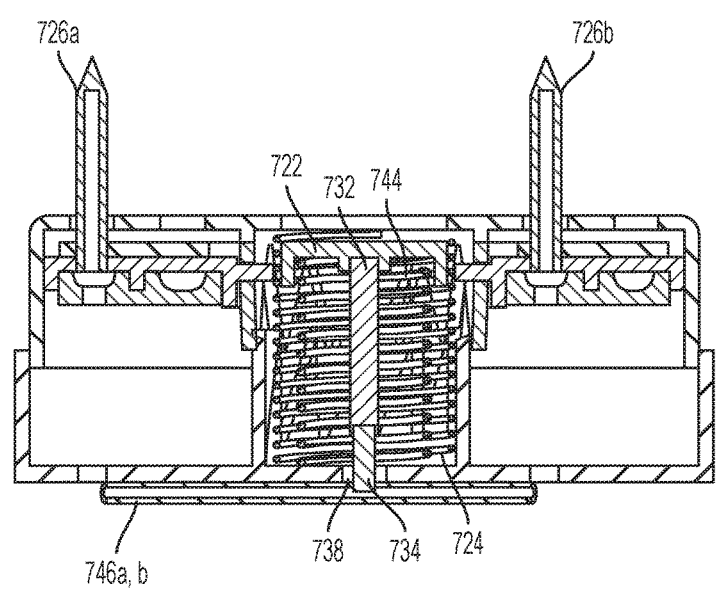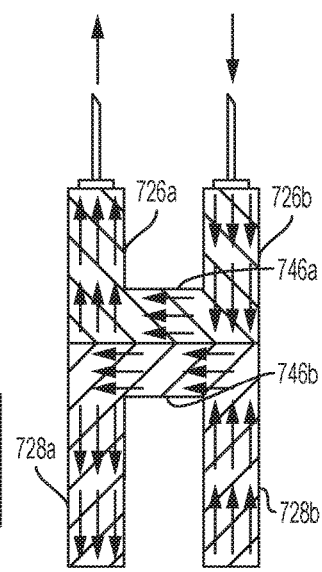
FIG. 9c    FIG. 9d

VASCULAR ACCESS PORT

FIELD OF THE INVENTION

The present invention relates generally to a vascular access port and, in particular, to a sub-cutaneous vascular access port that may include a needle that penetrates the skin, wherein the needle may extend or retract from the housing, and the needle may occupy a series of positions in the vascular access port upon repeated use.

BACKGROUND

Hematology patients, oncology patients, hemodialysis patients and other patients may be subject to frequent infusion treatments delivering pharmaceuticals, blood, nutrients, contrasting agents and other compositions. Frequent "needle sticks" and the duration of infusion time may make receiving such treatments uncomfortable and creates scarring and added discomfort to the patient. Vascular access ports are medical devices that may be inserted beneath the skin and may reduce the discomfort associated with such treatments. A port may include an access point, such as a septum, into which a needle may be inserted. A port may also include a catheter, which may be inserted into a vein, such as a jugular vein, subclavian vein or superior vena cava. The septum may be formed of a self-healing silicone material that may be punctured multiple times with a relatively low loss in the integrity of the septum. However, a clinician needs to properly target the access port and a risk of infection may exist as a needle extending into the skin may drag bacteria from the skin into the port.

SUMMARY OF THE INVENTION

An implantable vascular access port is described for providing repeated therapy to a patient in need of such therapy, wherein the access port, upon repeated use, presents each time an access needle at a new location so as to minimize scarring injury to the skin of the patient. The vascular access port may include a body, a cover with a plurality of openings, at least one needle with a tip and a shaft, the shaft defining a lumen, a needle elevator mechanism to operate the position of the at least one needle in at least a retracted position in which the at least one needle is disposed in the body and the needle tip below the cover and an extended position in which the at least one needle is protruding through at least a first one of the openings, and a needle shift mechanism to move the at least one needle from a first position in which the needle is aligned with a first one of the openings, to a second position in which the needle is aligned with a second one of the openings.

In certain embodiments, the access port may include a holder having the at least one needle disposed thereon and helical threads and the elevator mechanism may include helical threads positioned to engage with the thread of the holder. In some embodiments, the elevator mechanism may include a cylinder having thread in an interior surface, the needles being disposed inside the cylinder. In some embodiments, the elevator mechanism may include a rod having thread on an exterior surface, the needles being disposed beside the rod. In some other embodiments, the elevator mechanism may include at least one magnet. In some embodiments, the at least one magnet is a permanent magnet, or an electromagnet.

In certain embodiments, the needle shift mechanism may include a rotatable surface and at least one guide rod, the guide rod guiding the motion of the needle when the needle is being extended or retracted, and positioning the needle from the first position to the second position. In some embodiments, the needle shift mechanism may further include a slot and pin combination to position the needle at one of the at least first and second position. In some embodiments, the needle shift mechanism may further include a ratchet mechanism to position the needle at one of the at least first and second position.

In certain embodiments, the access port may also include a button that engages the needle shift mechanism to position the needle at one of the at least first to a second position. In certain embodiments, the needle shift mechanism can move the at least one needle from about six to about twelve positions. In some embodiments, at least one of the positions is a maintenance position which provides access to a replaceable part of the access port.

In certain embodiments, the access port may also include at least a valve to close flow of fluid through the at least one needle. In some embodiments, the access port may also include at least two needles and two valves, and a first channel bridging the two needles, wherein the valves close or open flow of fluid between the first channel and the at least two needles. In some embodiments, the access port may also include at least two vascular catheter inlets and a second channel bridging the two catheter inlets, wherein the valves close or open flow of fluid between the first channel and the at least two needles and between the second channel and the at least two vascular catheter inlets.

In a certain embodiment, an access port according to the invention may include a body defining at least two recesses for defining at least a first position and a second position, a cover with a plurality of openings, at least one needle including a tip and a shaft, the shaft defining a lumen, a cylinder having threads on an interior surface with the needles disposed inside the cylinder, a holder having the at least one needle disposed thereon and threads disposed to engage the threads of the cylinder, at least one magnet engaged with the cylinder to operate the position of the at least one needle in at least a retracted position in which the at least one needle is disposed in the body and the needle tip below the cover and an extended position in which the at least one needle is protruding through at least a first one of the openings; and a base plate disposed in the body and having at least one flexible resilient prong engaging at least one of the at least two recesses of the body, the base plate engaging the at least one needle to move the at least one needle from the first position in which the needle is aligned with a first one of the openings, to the second position in which the needle is aligned with a second one of the openings. In some embodiment, the base plate may further include at least a guide rod for engaging the at least one needle from the first position to the second.

In another embodiment, an access port according to the invention may include a body defining at least two recesses for defining at least a first position and a second position, a cover comprising a plurality of openings, at least one needle with a tip and a shaft, the shaft defining a lumen, a rod disposed along an axis of rotation of the access port and having threads on an exterior surface, a holder having the at least one needle disposed thereon and threads disposed to engage the threads of the rod, at least one magnet engaged with the rod to operate the position of the at least one needle in at least a retracted position in which the at least one needle is disposed in the body and the needle tip below the cover and an extended position in which the at least one needle is protruding through at least a first one of the openings, and a base plate disposed in the body and having at least one flexible resilient prong engaging at least one of the at least two recesses of the body, the base plate engaging the at least one needle to move the at least one needle from the first position in which the needle is aligned with a first one of the openings, to the second position in which the needle is aligned with a second one of the openings. In some embodiments, the base plate may further include at least a guide rod for engaging the at least one needle from the first position to the second.

In some other embodiments, the access port may include a body, a cover including a plurality of openings at least one needle having a tip and a shaft, the shaft defining a lumen, a holder for carrying the at least one needle inside the port, a ratchet unit disposed along an axis of the access port and having a bottom portion having at least two teeth and processes and having a top portion defining at least two teeth and processes, the bottom teeth and processes capable of engaging the top teeth and processes defining at least a first position and a second position, a first button engaging the holder to operate the position of the at least one needle in at least a retracted position in which the at least one needle is disposed in the body and the needle tip below the cover and an extended position in which the at least one needle is protruding through at least a first one of the openings, and a second button engaging the ratchet unit to move the at least one needle from the first position in which the needle is aligned with a first one of the openings, to the second position in which the needle is aligned with a second one of the openings. In some embodiments, the top ratchet portion may further include at least two slots for engaging at least one pin, wherein when the pin is sliding along one of the slot, the at least one needle is raised or lowered, and when the pin is shifted from one of the slot to the other one, the at least one needle is shifted from the first position to the second position.

In yet other embodiments, the access port may include a body, a cover comprising a plurality of openings, at least two needles, each comprising a tip and a shaft, the shaft defining a lumen, a holder for carrying the needles inside the port, a ratchet unit disposed along an axis of the access port and having a bottom portion having at least two teeth and processes and having a top portion defining at least two teeth and processes, the bottom teeth and processes capable of engaging the top teeth and processes defining at least a first position and a second position, a magnet engaging the holder to position the needles from at least a retracted position in which the needles are disposed in the body and the needle tips below the cover to an extended position in which the needles are engaged through at least a first two of the openings, a coil spring to operate the holder to position the needles from at least an extended position in which the needles are engaged through at least two openings to a retracted position in which the needles are disposed in the body and the needle tips below the cover, at least two valves, a first channel bridging the two needles, wherein the valves close or open flow of fluid between the first channel and the at least two needles, at least two vascular catheter inlets, and a second channel bridging the two catheter inlets, wherein the valves close or open flow of fluid between the first channel and the at least two needles and between the second channel and the at least two vascular catheter inlets; and a button engaging the holder to move the at least one needle from the first position in which the needle is aligned with a first one of the openings, to the second position in which the needle is aligned with a second one of the openings.

In yet some embodiments, there is provided a system to access the vasculature of a patient. The system may include an access port and an activator as described below. The access port may include a body defining at least two recesses for defining at least a first position and a second position, a cover comprising a plurality of openings, at least one needle comprising a tip and a shaft, the shaft defining a lumen, a cylinder having threads on an interior surface, the needles being disposed inside the cylinder, a holder having the at least one needle disposed thereon and threads disposed to engage the threads of the cylinder, at least one magnet engaged with the cylinder to operate the position of the at least one needle in at least a retracted position in which the at least one needle is disposed in the body and the needle tip below the cover and an extended position in which the at least one needle is protruding through at least a first one of the openings, and a base plate disposed in the body and having at least one flexible resilient prong engaging at least one of the at least two recesses of the body, the base plate engaging the at least one needle to move the at least one needle from the first position in which the needle is aligned with a first one of the openings, to the second position in which the needle is aligned with a second one of the openings. The actuator may include a magnet, for positioning over the skin of a patient above the implanted access port. In some embodiments, the actuator magnet is an electromagnet.

In yet other embodiments, there is provided a system to access the vasculature of a patient. The system may include an access port and an activator as described below. The access port may include a body defining at least two recesses for defining at least a first position and a second position, a cover comprising a plurality of openings, at least one needle comprising a tip and a shaft, the shaft defining a lumen, a rod disposed along an axis of rotation of the access port and having threads on an exterior surface, a holder having the at least one needle disposed thereon and threads disposed to engage the threads of the rod, at least one magnet engaged with the rod to operate the position of the at least one needle in at least a retracted position in which the at least one needle is disposed in the body and the needle tip below the cover and an extended position in which the at least one needle is protruding through at least a first one of the openings, and a base plate disposed in the body and having at least one flexible resilient prong engaging at least one of the at least two recesses of the body, the base plate engaging the at least one needle to move the at least one needle from the first position in which the needle is aligned with a first one of the openings, to the second position in which the needle is aligned with a second one of the openings. The actuator may include a magnet, for positioning over the skin of a patient above the implanted access port. In some embodiments, the actuator magnet is an electromagnet.

BRIEF DESCRIPTION OF THE DRAWINGS

The above-mentioned and other features of this disclosure, and the manner of attaining them, may become more apparent and better understood by reference to the following detailed description of embodiments described herein taken in conjunction with the accompanying drawings, wherein:

FIG. 2a illustrates a cross-sectional view of an example of a vascular access port contemplated herein paired with an actuator, showing an example of a ratcheting mechanism;

FIG. 3b illustrates a side view of an example of the ratcheting mechanism as shown in FIG. 3a;

FIGS. 3c to 3e illustrate cross-sectional views of the ratcheting system various configurations according to the vascular access port as shown in FIG. 3a;

FIG. 5a illustrates a perspective view of a vascular access port as shown in FIG. 3a;

FIG. 5b illustrates a side view of the operation of the needles of a vascular access port as shown in FIG. 5a, in a blood flow mode;

FIG. 5c illustrates a perspective view of a vascular access port as shown in FIG. 5a;

FIG. 5d illustrates a side view of the operation of the needles of a vascular access port as shown in FIG. 5a, in a needle-cleaning mode;

FIG. 6 illustrates a cross-sectional view of an example of a vascular access port contemplated herein paired with an actuator, with the needles in the retracted position;

FIG. 8a illustrates a side view of an example of a ratcheting system according to the vascular access port shown in FIGS. 7c-d;

FIGS. 8b to 8d illustrate side views of the ratcheting system various configurations as shown in FIG. 8a;

FIG. 9a illustrates a cross-section view of a vascular access port as shown in FIGS. 7a to 7d, in a blood flow mode;

FIG. 9b illustrates a side view of the operation of the needles of a vascular access port as shown in FIG. 9a, in a blood flow mode;

FIG. 9c illustrates a perspective view of a vascular access port as shown in FIGS. 7a to 7b, in a needle-cleaning mode;

FIG. 9d illustrates a side view of the operation of the needles of a vascular access port as shown in FIGS. 9c, in a needle-cleaning mode;

DETAILED DESCRIPTION

Figure 1A:
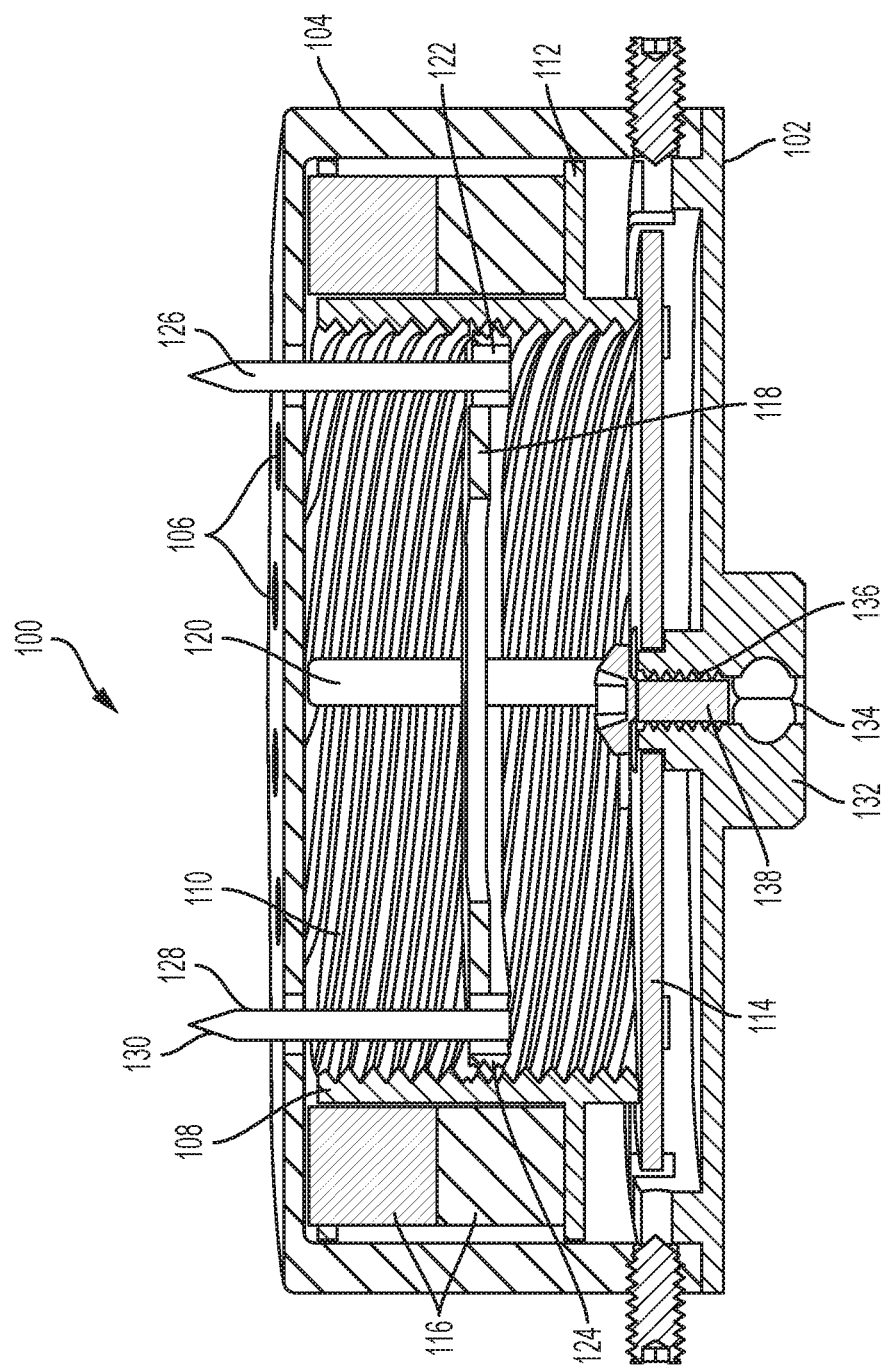
FIG. 1a illustrates a cross-sectional view of an example of a vascular access port contemplated herein, with the needles in the partially extended position.

It is to be understood that this disclosure is not limited in its application to the details of construction and the arrangement of components set forth in the following description or illustrated in the drawings. The embodiments herein are capable of other embodiments and of being practiced or of being carried out in various ways.

Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

Spatial references such as "above," "below," "top," "bottom," "horizontal," "vertical," "right," "left," and the like are meant to be understood in relation to the orientation of the device and parts thereof as illustrated in the figure being described, and are interchangeable upon spatial reorientation of the device.

Embodiments herein may refer to motion of moving parts as clockwise or counter-clockwise. Such embodiments should not be regarded as limiting of the invention as mirror-image embodiments can be adapted to perform the same operation or function in a reverse sense of motion, counterclockwise or clockwise as appropriate.

The present invention relates generally to a vascular access port and, in particular, to a sub-cutaneous vascular access port connected to a blood vessel, body cavity or organ of a patient via one or more internal catheters. The vascular access port may include at least one extendable/retractable needle. For certain medical applications, such as hemodialysis, two needles are required for the exit of blood from the patient and return of the clean blood to the patient. The embodiments of the vascular access ports described herein focusing on ports having two needles are equally applicable to ports having one needle, or more than two needles. The needle(s) may puncture through the skin of a patient, providing access to the port. A catheter or other device may be affixed to the needle(s) protruding from the port and through the skin of the patient to deliver a composition to the patient. The needle(s) may also puncture a vial stopper to deliver a composition stored in the vial.

In general, the vascular access port provides one or more retractable needles operated by an elevator mechanism. In addition, the vascular access port also provides multiple positions for the one or more needles to occupy at each of the multiple uses, so that the one or more needles will extend at a new position for each use. The one or more needles are shifted from a first position to the next by a shifting mechanism inside the port. The elevator mechanism may be operated with an external actuator, or with an actuator within the port. Similarly, the shifting mechanism may be operated with an external actuator, or with an actuator within the port.

Examples of suitable external actuators may include permanent magnets or electromagnets. Examples of suitable internal actuators may include buttons, levers, switches and the like.

Figure 1B:
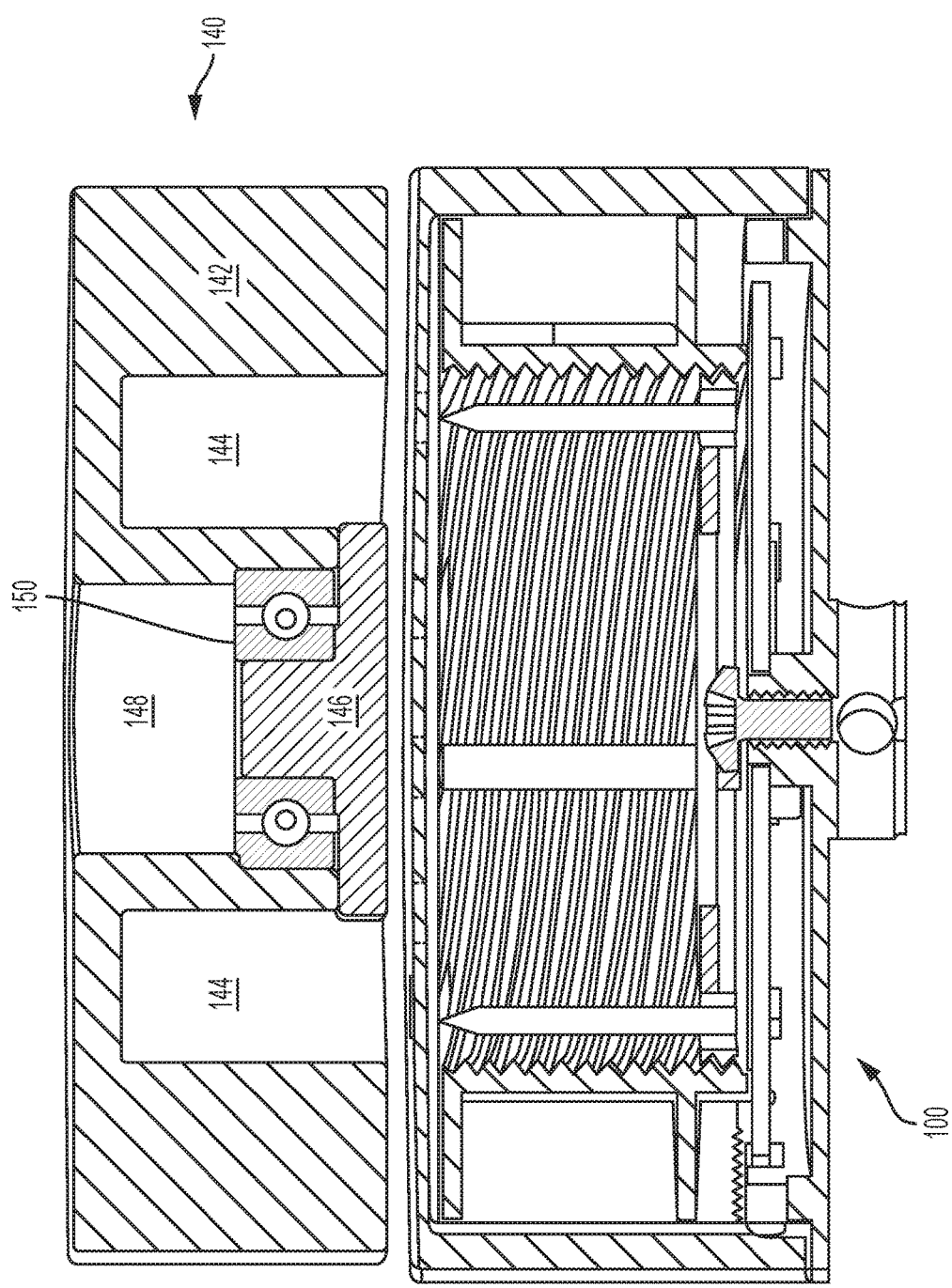
FIG. 1b illustrates a cross-sectional view of the vascular access port of FIG. 1a paired with an actuator, with the needles in the retracted position.

FIGS. 1a and 1b illustrate an example of a vascular access port 100 including two needles in the extended and retracted positions, respectively. FIG. 1a illustrates the access port 100 which may generally include a base plate 102 supporting a cover 104. The cover 104 may have on the top surface a series of openings 106 to allow the passage of needles 126 through the top in and out of the port. The vascular access port 100 may be contained in a housing that prevents access of body fluids or ingrowth of body tissue into the port. The housing may be made of a self-healing material, such as silicone. Alternatively, the cover 104 may be made of a self-healing material, and the needles 126 pierce through the cover 104. The openings created in the self-healing material close upon retraction of the needles so that the vascular access port 100 remains impervious to body fluids and ingrowth of body tissue. The base plate 102 also supports a floor plate 114 onto which rests a cylinder 108. The cylinder 108 may include threads 110 in the interior, and, on the periphery, flanges 112 to receive permanent magnets 116.

The needles 126 are supported within the interior of the cylinder 108 by a needle plate 118. One or more guide rods 120 maintain the axial position of the needles 126 in the vascular access port 100 during the operation of the vascular access port 100 that elevates and retracts the needles, in and out of the vascular access port 100. The needle plate 118 may have threads 124 on the periphery that engage the threads 110 of the cylinder. The magnets 116, the cylinder 108 with the threads 110 and flanges 112, the needle plate 118 and needle-plate threads 124 together are parts of the elevator mechanism. The needles 126 may include a shaft 128 for connecting through a fluid path with an internal catheter accessing the blood vessel (not shown), and a removable tip 130 which allows access to the lumen of the needles 126 for the passage of fluids or blood. The needle 126 may be made of medical grade steel, or of a ferromagnetic material, or may include a ferromagnetic material at the tip 130.

The base plate 102 includes a hub 132 that serves as the connection area to which catheters or other devices used may be attached. Details of such connections are well known and not illustrated here. A screw 138, using thread 136 to retain the screw, and a seal 134 serve to retain the plate 114 from moving axially while allowing rotation. Other means well known in the art may be used in the place of the parts described herein to provide the described functions.

FIG. 1b illustrates the vascular port 100 paired with an actuator 140. The actuator 140 may include permanent magnets or an electromagnet (not shown) in body 142 a circular chamber 144 that accommodates the needle 126 in the expanded configuration. The actuator 140 may include bearings 150 disposed in a central bore 148. The rotational support 146 provides a spacing to keep the main body 142 from overly contacting the surface of the skin or sterile covering for the skin of the patient and easing rotation of the actuator 140.

In operation, the vascular access port 100 is positioned under the skin of a patient in need of repeated vascular access. Medical personnel position the actuator 140 onto the skin above the implanted vascular access port 100 and actuate the magnet or magnets placed within body 142 which engage the elevator mechanism inside the port. The elevator mechanism includes the magnets 116, the cylinder 108, the needle plate 118 and needle-plate threads 124. The actuator magnets engage with the magnets 116 within the port and induce rotation of the cylinder 108. The rotation of the cylinder 108 causes the sliding of the needle-plate threads 124 along the threads 110 of the cylinder, moving the needles 126 upward or downward depending on the direction of the rotation of the cylinder 108. FIG. 1b illustrates the vascular access port 100 with the needles 126 in the retracted position before actuation of the vascular port 100. FIG. 1a illustrates the vascular access port 100 with the needles 126 in the partially extended position with the tips 130 of the needles 126 slightly protruding from the cover 104.

The vascular access port 100 may also include a shifting mechanism that, upon full retraction of the needles into the vascular port 100, shifts the axial position of the needles 126 inside the cylinder 108 such that upon reactivation of the vascular access port 100, the needles 126 will protrude from the port at a new location. One example of such mechanism is described below and illustrated in FIGS. 1c and 1d.

Figure 1C:
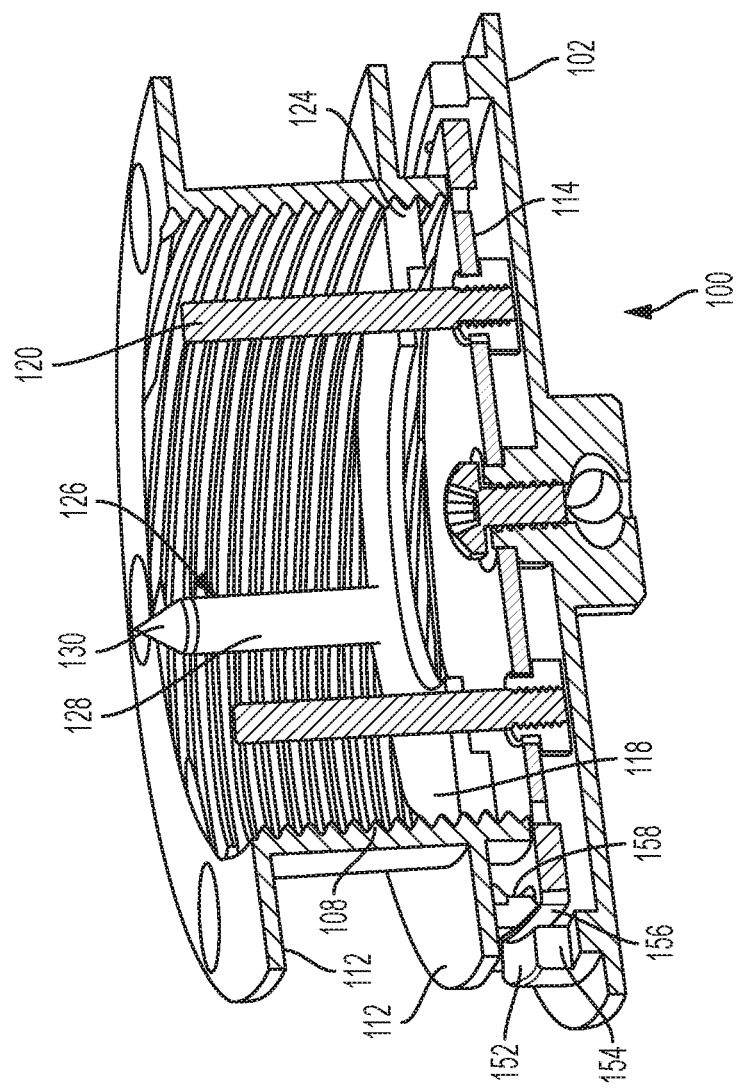
FIG. 1c illustrates a cross-sectional view of the internal parts of the vascular access port of FIG. 1a, without the cover and the magnets.
Figure 1D:
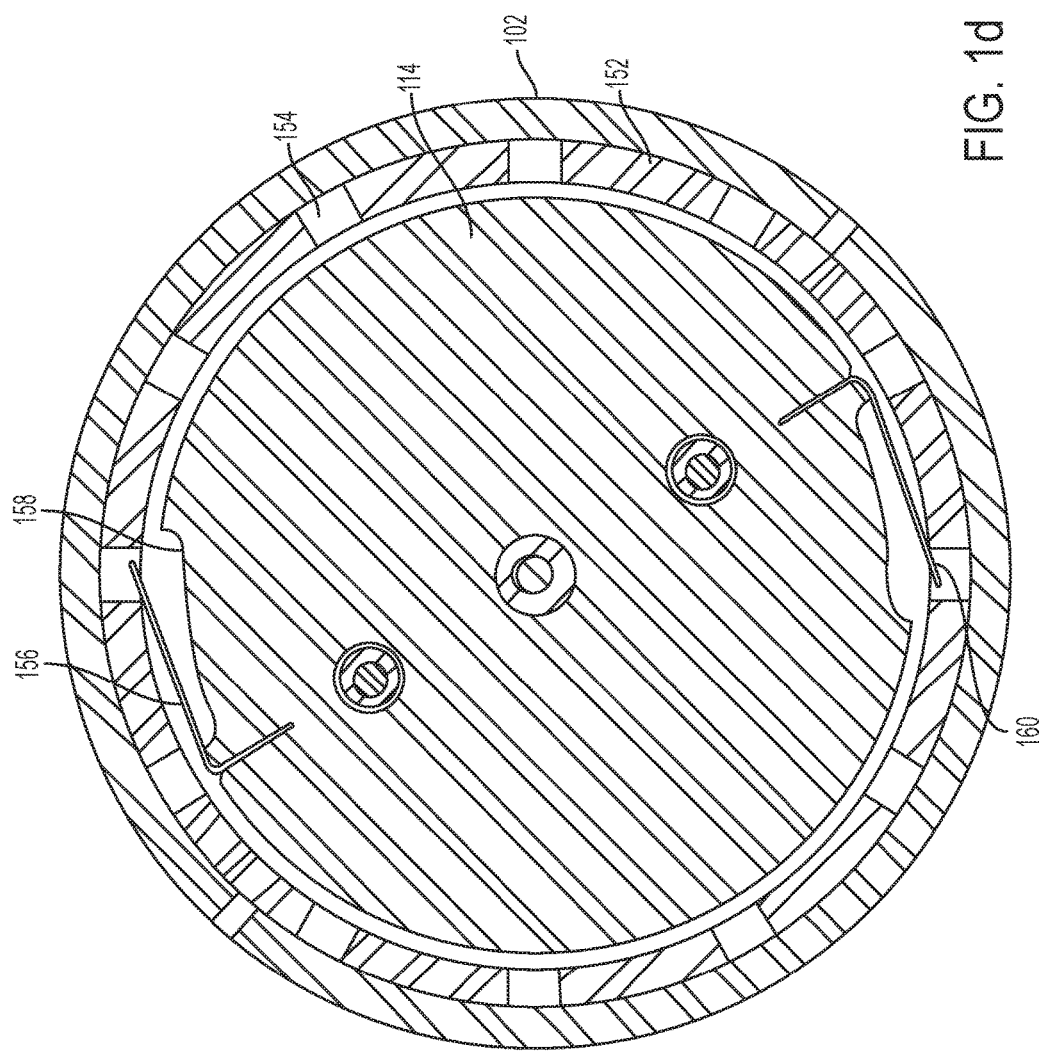
FIG. 1d illustrates a cross-sectional top view of the vascular access port of FIG. 1a, at the base plate level showing detail of the ratcheting mechanism.

Referring to FIGS. 1c and 1d, the vascular access port 100 may include a ratcheting mechanism that moves the position of the needles within the vascular access port at the end of each use, so that on the next use of the vascular access port the needles will pierce the skin at a new location and minimize the patient discomfort due to excessive scarring when the needles exit the skin repeatedly at the same location. In FIG. 1c, the base plate 102 may include a circular rim 152 near the edge of the base plate and surrounding the floor plate 114. The rim 152 may include a defined number of slots 154, which predetermine the various axial positions that the needles 126 may occupy in the vascular access port 100. There may be from two to twenty, most commonly six to twelve slots 154 that may be spaced apart at regular intervals around on the rim 152 depending on the intended repeated use of the vascular access port 100. In the displayed embodiment, the rim includes twelve positions which afford six positions for the two needles 126 to pierce the skin of a patient at a new location. One or more flexible and resilient members 156 connected to or integral to the floor plate 114 engage one or more of the slots 154 at an angle so that the extremity 160 abuts a vertical wall of the slot 154 in which it resides and prevents the floor plate 114 from rotating in the clockwise direction when the needles 126 are being raised, but can rotate in the counter-clockwise direction once the needle 126 have been fully retracted and the needle plate 124 engages with the floor plate 114. At this point, the floor plate 114 has moved beyond the threaded section of cylinder 108 and rotates it counter-clockwise from a first position to the next available position afforded by the slots 154. Alternately, the direction of the threads of cylinder 108 and the design of the ratcheting mechanism shown in FIG 1*d* could be reversed to make the device turn in the opposite way.

The ratcheting mechanism may operate by friction of the needle plate 124 onto the floor plate 114, or by the engagement of a pin/notch combination (not shown) positioned between the needle plate 124 and the floor plate 114 so as to engage one another once the needle plate 124 has reached is lowermost position in the vascular access port 100 against the floor plate 114. Due to a ratcheting mechanism such as one detailed in FIG. 1*d*, rotation of the floor plate will prefer to stop at one of the defined positions for later needle extraction. The ratcheting mechanism may provide an auditory signal when it reaches one of the defined positions. The design allows the clinician to further advance the needles to other further positions if it is so desired to avoid a sensitive location for the patient.

The resilient member may be a spring, as illustrated in FIG. 1*d*, positioned near a recess 158 in the floor plate 114, or an integral portion of the floor plate 114, such as a protrusion or by any other means, ratcheting mechanisms are well known, an alternate example is shown in FIGS. 2*a* to 2*d* below.

Figure 2B:
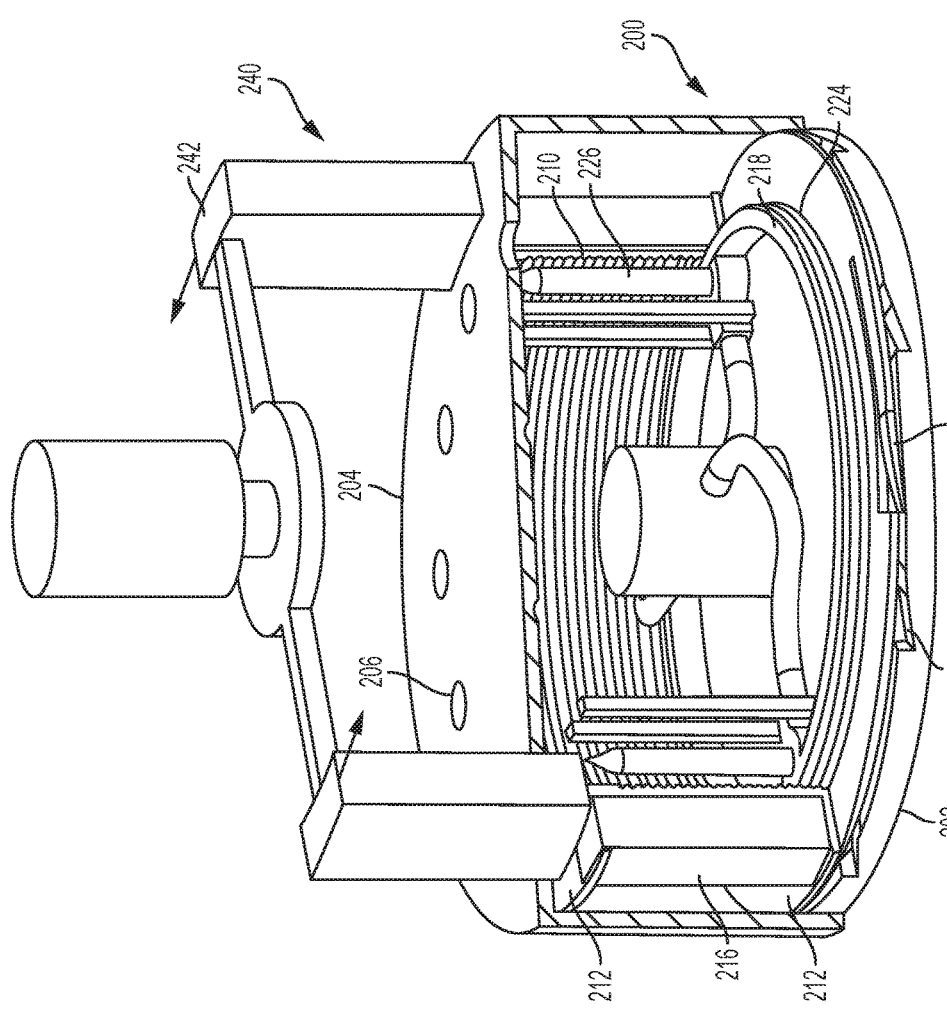
FIGS. 2b to 2d illustrate cross-sectional views of the ratcheting mechanism of FIG. 2a, in various configurations.

FIGS. 2*a* to 2*d* illustrate another example of a vascular access port 200 according to the invention with an alternate ratcheting mechanism. FIG. 2*a* illustrates the vascular access port 200 which may generally include a base plate 202 supporting a cover 204. The cover 204 may have on the top surface a series of openings 206 to allow the passage of needles 226 through the top, in and out of the vascular access port 200. The vascular access port 200 may be contained in a housing that prevents access of body fluids or ingrowth of body tissue into the vascular access port. The housing may be made of a self-healing material, such as silicone. Alternatively, the cover 204 may be made of a self-healing material, and the needles 226 pierce through the cover 204. The openings created in the self-healing material close upon retraction of the needles so that the vascular access port 200 remains impervious to body fluids and ingrowth of body tissue. The base plate 202 also supports a floor plate 214 onto which rests a cylinder 208. The cylinder 208 may include threads 210 in the interior, and on the periphery, flanges 212 to receive permanent magnets 216.

The needles 226 are supported within the interior of the cylinder 208 by a needle plate 218. One or more guide rods 220 maintain the axial position of the needles 226 in the vascular access port 200 during the operation of the vascular access port 200 that elevates and retracts the needles, in and out of the vascular access port 200. The needle plate 218 may have threads 224 on the periphery that engages the threads 210 of the cylinder 208. The magnets 216, the cylinder 208 with the threads 210 and flanges 212, the needle plate 218 and needle-plate threads 224 together are parts of the elevator mechanism. The needles 226 may each include a shaft 228 for connecting with a flexible linking tube 232 connected a central post 234. The central post 234 may include channels that connect to catheters that access the blood vessel (not shown). The needles 226 may also include a removable tip 230 which allows access to the lumen of the needle for the passage of fluids or blood.

Figure 2C:
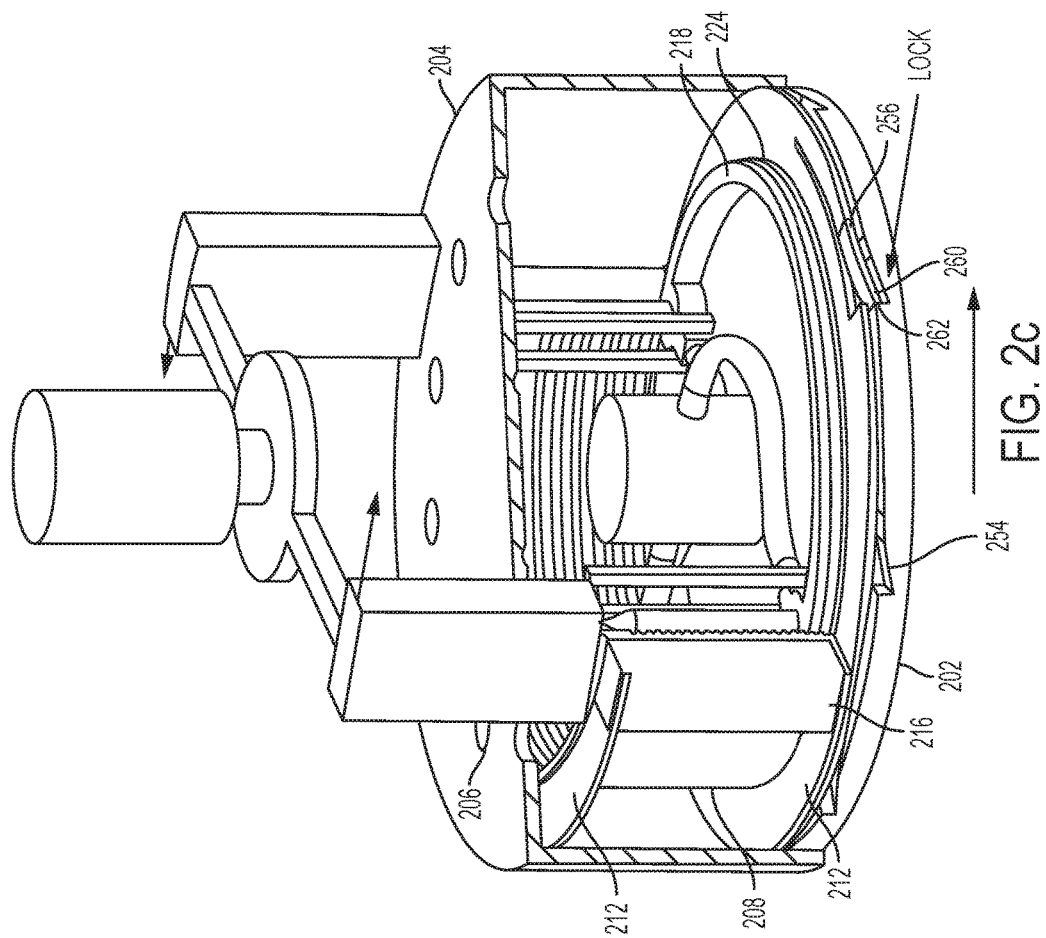
Figure 2D:
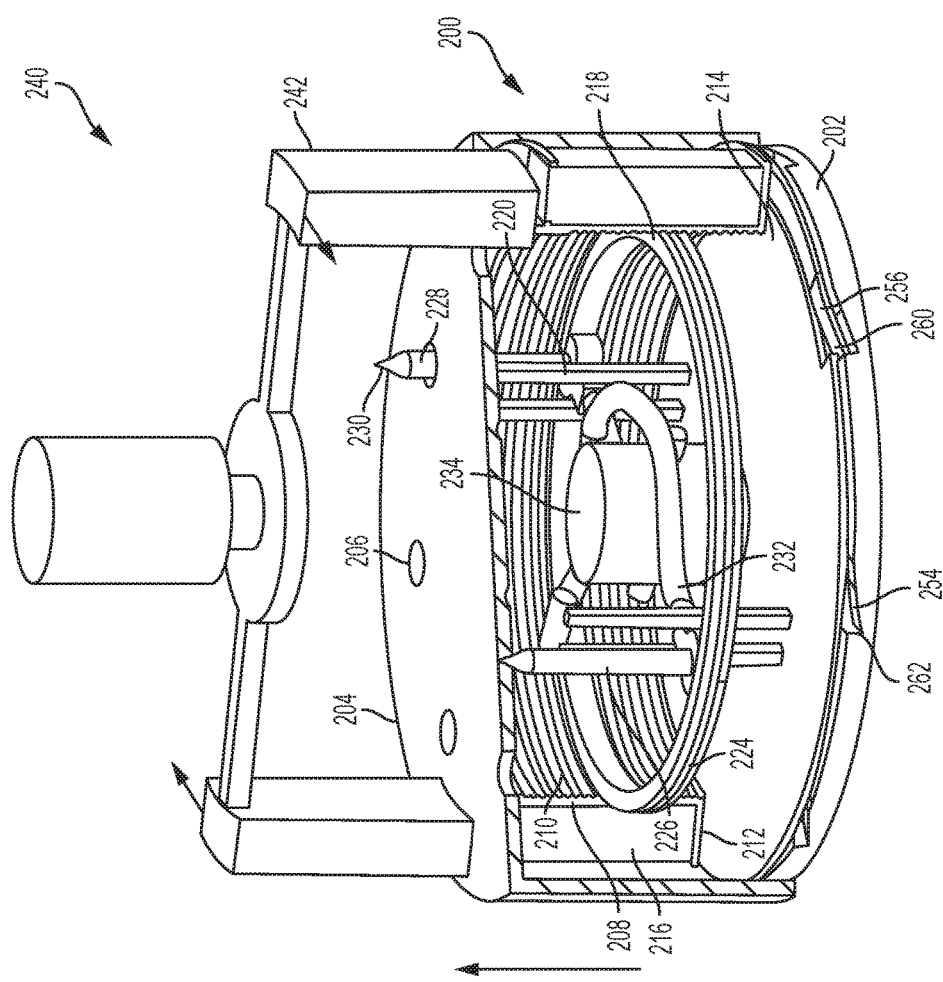

In operation, the vascular access port 200 is positioned under the skin of a patient in need of repeated vascular access. Medical personnel position the actuator 240 onto the skin above the vascular access port 200 and activate the magnets 242, which engage engage the elevator mechanism inside the port. The elevator mechanism includes the magnets 216, the cylinder 208, the cylinder threads 210 the needle plate 218 and needle-plate threads 224. The activator magnets engage with the magnets 216 and induce rotation of the cylinder 208. The rotation of the cylinder 208 causes the sliding of the needle plate threads 224 along the treads 210 of the cylinder 208, moving the needles 226 upward or downward depending on the direction of the rotation of the cylinder 208. FIG. 2*a* illustrates the vascular access port 200 with the needles 226 in the retracted position at a first axial position at the end of the actuation of the vascular port 200 after use. FIG. 2*b* illustrates the vascular port 200 with the needles 226 in transit to a second axial position. FIG. 2*c* illustrates the vascular access port 200 with the needles 226 at the second axial position.

FIGS. 2*a-d* illustrate the sequence of motions generated by the shifting mechanism inside the vascular access port 200 that moves the needles from a first axial position (FIG. 2*a*) to a second axial position (FIG. 2*c*). In FIG. 2*a*, the base plate 202 may include at the edge 252 a defined number of slots 254 which predetermine the various positions that the needles 226 may occupy in the vascular access port 200. There may be from two to twenty, most commonly six to twelve slots 254 that may be spaced apart at regular intervals around on the edge 252 depending on the intended repeated use of the vascular access port 200. In the displayed embodiment, the edge includes twelve slots which afford six axial positions for the two needles 226 to pierce the skin of a patient at a new location. One (or more) flexible and resilient bent portion 256 integral to the floor plate 214 engages one of the slots 254 at an angle so that the extremity 260 abuts a vertical wall 262 of the slot 254 in which it resides and prevents the floor plate 214 from rotating in the clockwise direction when the needles 226 are being raised, but can rotate in the counter-clockwise direction once the needles 226 have been fully retracted and the needle plate 224 engages with the floor plate 214. At this point, the floor plate 214 has moved beyond the threaded section of cylinder 208 and it rotates counter-clockwise from a first position to the next available position afforded by the slots 254. The ratcheting mechanism may provide an auditory signal when it reaches one of the defined positions. The design allows the clinician to further advance the needles to other further positions if it is so desired, such as to avoid a sensitive location for the patient.

The ratcheting mechanism may operate by friction of the needle plate 224 onto the floor plate 214, or by the engagement of a pin/notch combination (not shown) positioned between the needle plate 224 and the floor plate 214 so as to engage one another once the needle plate 224 has reached is lowermost position in the vascular access port 200. Due to a ratcheting mechanism such as one detailed in FIG. 2*a*, rotation of the floor plate will prefer to stop at one of the defined positions for later needle extraction.

Figure 3A:
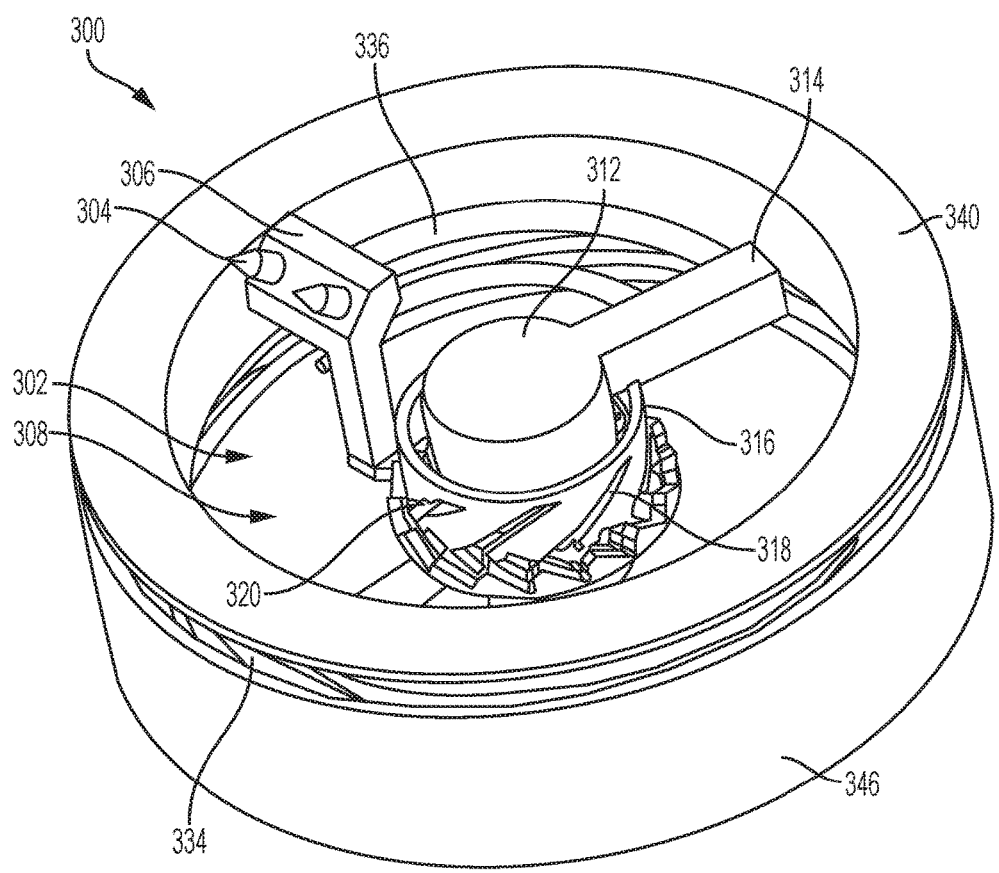
FIG. 3a illustrates a perspective view of an alternate example of a vascular access port contemplated herein, with the needles in the retracted position.
Figure 3B:
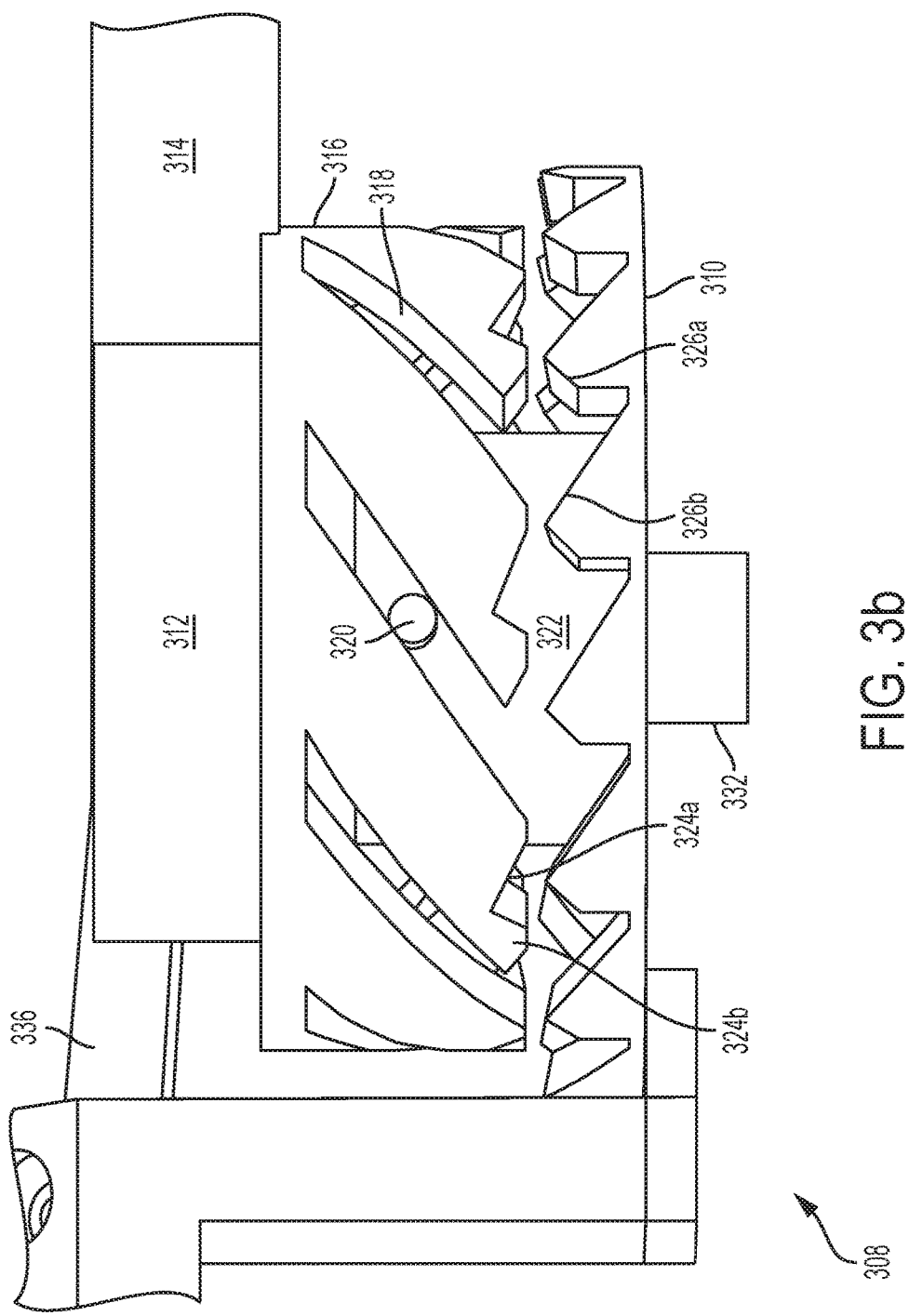

FIGS. 3*a* and 3*b* illustrate another example of a vascular access port 300. In this example, the cover has been removed to expose the elevator mechanism and needle-shifting mechanism 302. Inside the vascular access port 300, the needles 304 may be supported by an arm 306 that is connected to a bottom ratchet portion 310 of a ratcheting system 308 which are part of the shifting mechanism. The ratcheting system 308 is circular and disposed in the center of the vascular access port 300 over a central shaft 332 (shown in FIG. 3b). The ratcheting system 308 may also include a top ratchet portion 316 disposed above a bottom ratchet portion 310. The top ratchet portion 316 may have a cylindrical wall with a series of slits 318 for receiving a pin 320 which protrudes outwardly from a central cylinder 322 (shown in FIG. 3b) disposed over a central shaft 332. The ratcheting system 308 may include a button 312 disposed over the central cylinder 322. The button 312 may include an arm 314 that holds the needle shafts 336. The arm 314 contains channels connected to the needle shafts at one end and to the vascular catheters (not shown) at the other end. The button 312, the pin 320, the slits 318 and the central cylinder 322 together with the needle arm are part of the elevator mechanism.

When the button 312 is depressed by the medical personnel, it triggers the ratcheting system 308 to shift the position of the needles 304 up out of the arm 306. The ratcheting system 308 shifts the arm 306 clockwise forcing the needle shafts 336 to slide through slits 318 in the arm 306. Because the slits 318 are oblique, the needles are elevated. Referring to FIG. 3b, when the button 312 is depressed, the pin 320 slides in one of the slits 318, rotating the top portion 316 as the pin 320 shifts downward, as shown in this embodiment clockwise. The notches 324a,b of the top ratchet portion 316 engage with the notches 326a,b of the bottom ratchet portion 310 forcing the bottom ratchet portion 310 to rotate one notch at a time for each depression of the button 312, displacing with it the needle arm 306 and thus positioning the needles 304 at a new axial position. The needle arm (as shown in FIG. 3b) connects to the bottom ratchet portion 310. The needles 304 (not shown) are connected to the flexible tubing 336 that are then connected to the outer portions of arm 314. Within arm 314 are passages (not shown) that then direct flow for each needle to a connection to the cannula supplying each needle at the bottom of the vascular access port 300. The button arm 314 fits into a slot of the upper edge of the top ratchet portion 316, so as to move it rotationally along with the needles 304.

The coil spring 334 between the flange 340 of the cylinder 342 and body 346 serves to separate the top ratchet portion 316 from the bottom ratchet portion 310 until the button 312 is depressed.

FIGS. 3c to 3e illustrate various stages of the operation of the ratcheting system 308 of vascular access port 300 shown in FIG. 3a. In the first stage, shown in FIG. 3c, the top portion 316 and bottom portion 310 of the ratcheting system 300 are disposed inside a coil spring 340. A button 312 is connected to a pin 320 engaged in a slot 318 in the top portion 316. When the button 312 is depressed the first time, pin 312 travels down slot 318 from position 320a to 320b until it reaches the bottom of notch 326 of the bottom portion 310 where it stops downward progress at position 320c. Upon release of the button 312, the pin 320 shifts to notch 324 of the top portion 316 at position 320d where it lodges and maintains the button 312 in a depressed configuration as shown in FIG. 3d. Referring to FIG. 3e, when the button is depressed a second time, the pin 320 shifts to position 320e engaging notch 326' disposed clockwise of notch 326. Upon release of the button 312 again, the pin 320 shifts into adjacent slot 318' at position 320f of the top portion 316, disposed clockwise to slot 318 to settle at the top of slot 318' at position 320g. As the pin 320 travels from position 320a to 320g, the ratcheting system rotates counter-clockwise moving the needles into a new position inside the vascular access port 300.

Figure 4B:
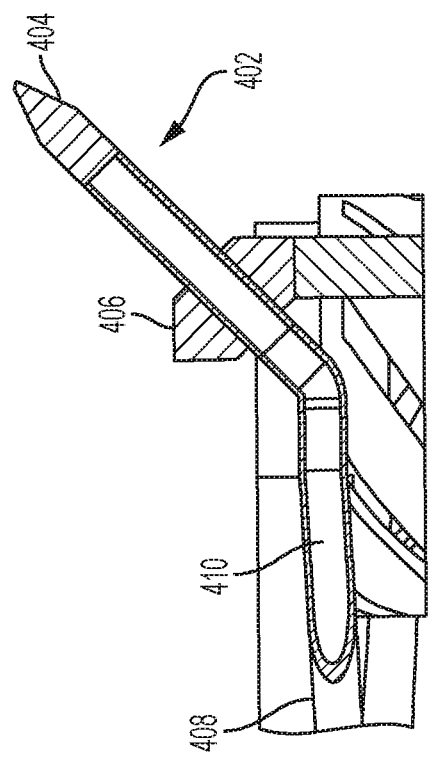
FIG. 4b illustrates a partial cross-sectional view of the needle arm of the vascular access port as shown in FIG. 3a, with the needles in the extended position.
Figure 4A:
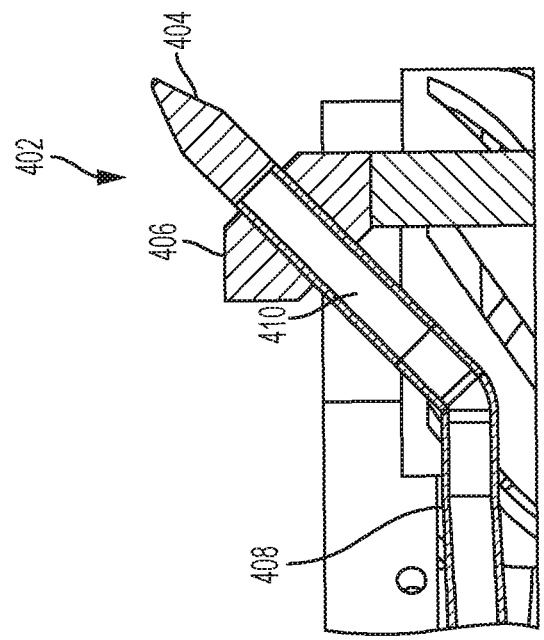
FIG. 4a illustrates a partial cross-sectional view of the needle arm of the vascular access port as shown in FIG. 3a, with the needles in the retracted position.

FIGS. 4a and 4b illustrate the retracted and extended position of the needles 402 in relation to the needle arm holder 406 with a portion of the needle shaft 408 in cross-section to show the lumen 410 of the needle. As the needle arm holder 406 rotates counter-clockwise, the proximal portion of the needle shaft 408 is pushed upward, lifting the tips 404 of the needles 402.

FIG. 5a illustrates a perspective view of the interior of the vascular access port as shown in FIG. 3a. A base 506 contains a large cylinder 508 having a flange 510 that is flush with the top rim of a smaller cylinder 512. The large cylinder 508 is propped in an upward position with a coil spring 514. In this configuration, the needles 502 and 504 operate in blood flow mode, as shown in FIG. 5b, where valve 520 of needle 504 is open and in a vertical position preventing access to top bridge 516 and bottom bridge 518. The same is observed for needle 502, where valve 522 of needle 502 is open and in a vertical position preventing access to top bridge 516 and bottom bridge 518. The flow of blood can thus exit needle 504 and enter needle 502 as when the vascular access port is used for hemodialysis of a patient with kidney failure.

FIG. 5c illustrates a configuration in which the outer cylinder 508 is depressed and flush to the base 506. In this configuration, the needles 502 and 504 operate in cleaning mode, as shown in FIG. 5d, where valve 520 of needle 504 and valve 522 of needle 502 are closed and prevent the blood flow in needles 504 and 502 creating a lower loop for the blood flow from catheter 526 to catheter 524 in bottom bridge 518, and allow access to top bridge 516 from the needles 504 and 502 for a cleansing solution, which may be used to prevent the formation of blood clots in the needles 502 and 504.

FIG. 6 illustrates an example of a vascular access port 600 including two needles 626 in the retracted position. The access port 600 may generally include a base plate 602 supporting a cover 604. The cover 604 may have on the top surface a series of openings 606 to allow the passage of needles 626 through the top in and out of the vascular access port 600. The vascular access port 600 may also be contained in a housing that prevents access of body fluids or ingrowth of body tissue into the vascular access port 600. The housing may be made of a self-healing material, such as silicone. Alternatively, the cover 604 may be made of a self-healing material, and the needles 626 pierce through the cover 604, The openings created in the self-healing material closes upon retraction of the needles so that the vascular access port 600 remains impervious to body fluids and ingrowth of body tissue. The base plate 602 also supports a floor plate 614 and a central rod 608 with threads 610.

The needles 626 are supported by a needle plate 618. One or more guide rods 620 maintain the axial position of the needles 626 in the vascular access port 600 during the operation of the vascular access port 600 that elevates and retracts the needles 626, in and out of the vascular access port 600. The needle plate 618 may have threads 624 at the center that engage the threads 610 of the central threaded rod 608. The needles 626 may include a shaft 628 for connecting, through a fluid path, with an internal catheter accessing the blood vessel (not shown), and a removable tip 630 which allows external access to the lumen of the needles 626 for the passage of fluids or blood.

Permanent magnets 616 are supported by a magnet plate 612. The magnet plate 612 may include a ball bearing system 615 to facilitate the rotation of the magnets in the vascular access port 600 while raising and retracting the needles 626. The magnets 616, the central rod 608 with the threads 610, the magnet plate 612, the needle plate 618 and needle-plate threads 624 together are part of the elevator mechanism.

In operation, the vascular port 600 is paired with an actuator 640. The actuator 640 may include a permanent magnet 642 supported by a magnet plate 644 and a handle 646.

In operation, the vascular access port 600 is positioned under the skin of a patient in need of repeated vascular access. Medical personnel position the actuator 640 onto the skin above the vascular access port 600 and rotate the magnets 642, which engage the elevator mechanism inside the port. The elevator mechanism includes the magnets 616, the central rod 608, the needle plate 618 and needle-plate threads 624. The actuator magnets engage with the magnets 616 and induce rotation of the central rod 608. The rotation of the central rod 608 causes the sliding of the needle-plate threads 624 along the treads 610 of the central rod 608, and with the help of the guide rods 628, moving the needles 626 upward or downward depending on the direction of the rotation of the central rod 608. The vascular access port 600 may also include a system that, upon full retraction of the needles 626 into the vascular port 600, shifts the axial position of the needles 626 inside the vascular access port 600 such that upon a subsequent activation of the vascular access port 600, the needles 626 will protrude from the vascular access port 700 at a new axial position.

As shown before in FIG. 6, such system may include a ratcheting mechanism that moves the position of the needles within the vascular access port at the end of each use, so that on the next use of the port the needles will pierce the skin at a new location. The base plate 602 may include at the edge 652 a defined number of slots 654 which predetermine the various positions that the needles 626 may occupy in the vascular access port 600. Two to twenty, most commonly six to twelve, slots 654 may be spaced apart at regular intervals around on the edge 652, depending on the intended repeated use of the vascular access port 600. In the displayed embodiment, the edge includes twelve positions which afford six positions for the two needles 626 to pierce the skin of a patient at a new location. A resilient bent portion 656 integral to the floor plate 614 engages one of the slots 654 at an angle so that the extremity 660 abut a vertical wall of the slot 654 in which it resides and prevents the floor plate 614 from rotating in the clockwise direction when the needles 626 are being raised, but can rotate in the counter-clockwise direction once the needles 626 have been fully retracted and the needle plate 624 engages with the floor plate 614. At this point, the floor plate 614 has moved beyond the threaded section of cylinder 608 and the floor plate 614 rotates counter-clockwise from a first position to the next available position afforded by the slots 654.

The ratcheting mechanism may operate by friction of the needle plate 618 onto the floor plate 614, or by the engagement of a pin/notch combination (not shown) positioned between the needle plate 624 and the floor plate 614 so as to engage one another once the needle plate 624 has reached is lowermost position in the vascular access port 600. Due to a ratcheting mechanism such as one detailed in FIG. 6, rotation of the floor plate will prefer to stop at one of the defined positions for later needle extraction.

Figure 7A:
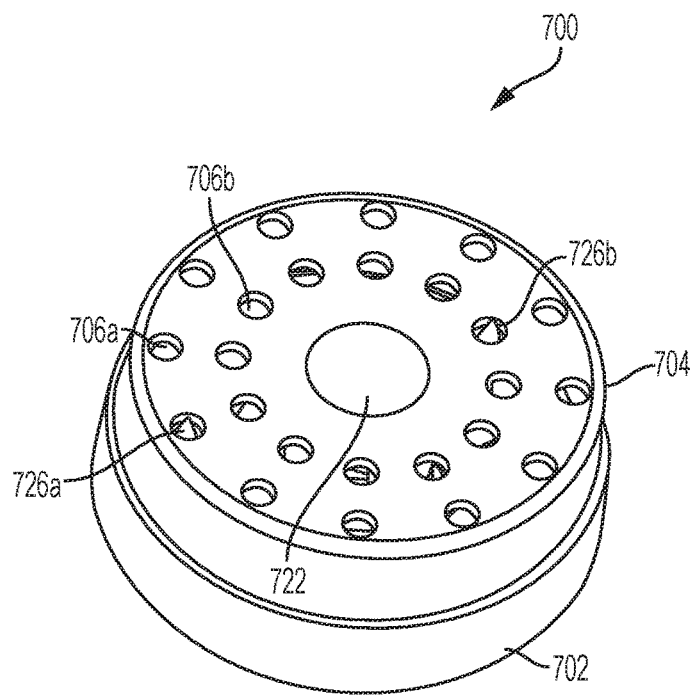
FIG. 7a illustrates a perspective view of an example of a vascular access port contemplated herein, with the needles in the retracted position.
Figure 7B:
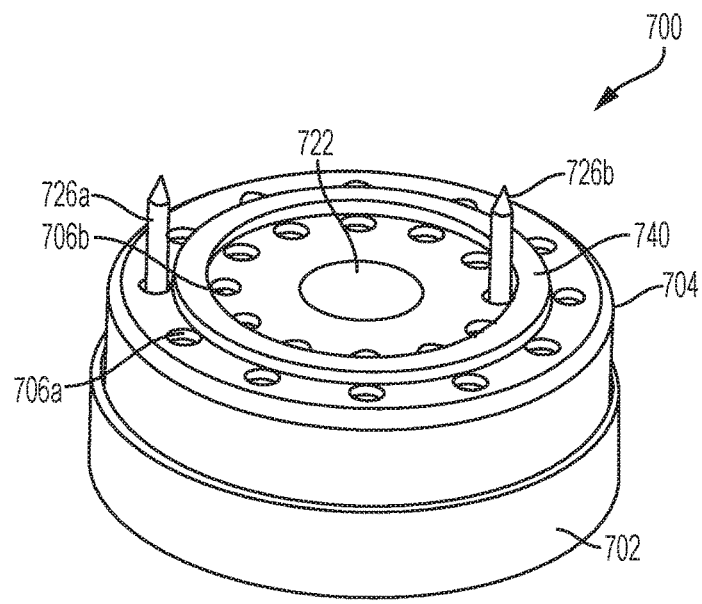
FIG. 7b illustrates a perspective view of an example of a vascular access port contemplated herein paired with an actuator, with the needles in the extended position.

FIGS. 7a and 7b illustrate another example of a vascular access port 700 with an elevator mechanism and needle shifting mechanism. The access port 700 may generally include a cupped body 702 supporting a cover 704. The cover 704 may have on the top surface a series of openings 706a,b to allow the passage of needles 726a,b respectively, through the top in and out of the vascular access port 700. The vascular access port 700 may also be contained in a housing that prevents access of body fluids or ingrowth of body tissue into the port. The housing may be made of a self-healing material, such as silicone. Alternatively, the cover 704 may be made of a self-healing material, and the needles 726a,b pierce through the cover 704. The openings created in the self-healing material closes upon retraction of the needles so that the vascular access port 700 remains impervious to body fluids and ingrowth of body tissue.

Figure 7C:
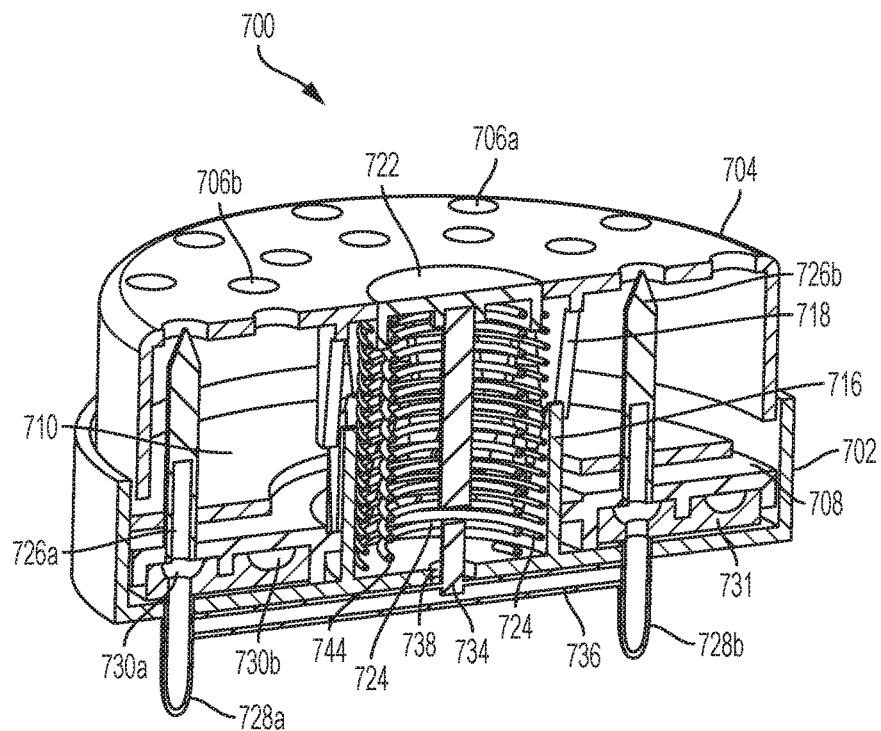
FIG. 7c illustrates a cross-sectional view of an example of the vascular access port shown in FIG. 7a, with the needles in the retracted position.

Referring to FIGS. 7b and 7c, inside the vascular access port 700, the needles 726a,b may be supported by a support plate 708. A circular ratcheting system is disposed in the center of the vascular access port 700. The ratcheting system may include a top ratchet portion 714 disposed above a bottom ratchet portion 712 (as shown in FIG. 8a). The top ratchet portion 714 may have a cylindrical wall separate or integral to the cover 704, with a series of downward pointing teeth 718. Similarly, the bottom ratchet portion 712 may have a cylindrical wall separate or integral to the base plate 702, with a series of upward pointing teeth 716.

The needle support plate 708 contains circular channels 730a,b in fluid communication with the lumen of needles 726a,b, respectively, at the bottom surface of the needle support plate 708, and in fluid communication with the lumen of the catheters 728a,b, respectively, that access the blood vessels of a patient. The circular channels may be defined by the bottom wall of the needle support plate 708 in the form of two grooves in the bottom surface in which are fitted a circular ring 731 having also two circular grooves, hence defining channels 728a,b.

Figure 7D:
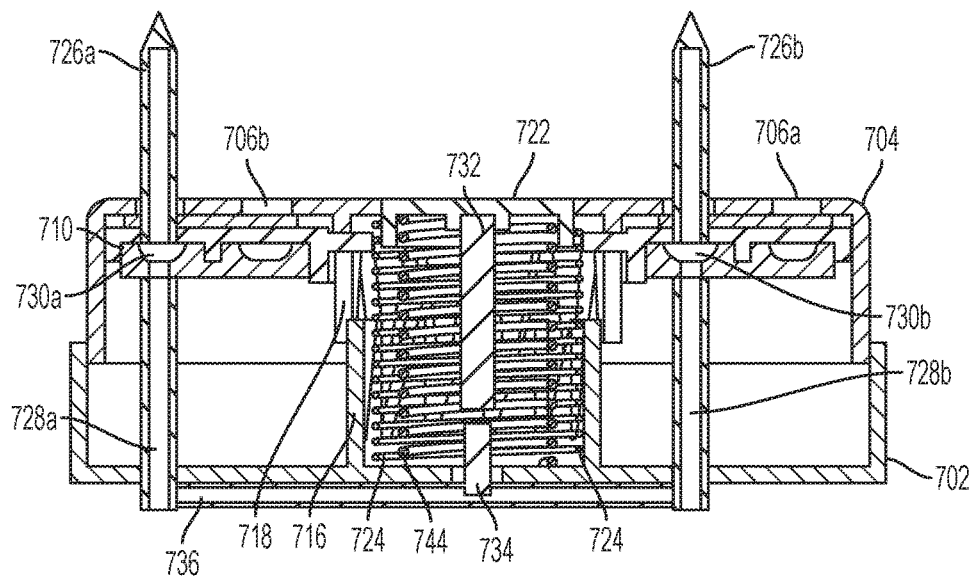
FIG. 7d illustrates a cross-sectional view of an example of the vascular access port shown in FIG. 7b, with the needles in the extended position.

Referring still to FIGS. 7b and 7d, when an external magnet 740, such as a permanent magnet or electromagnetic coil, is applied by the medical personnel on the skin of the patient over the vascular access port 700 (as shown in FIG. 7b), it activate the elevator mechanism by attracting the internal magnet 710, raising the needle support plate 708, along with needles 726a,b and through respective openings 706a,b. Removal of the permanent magnet, or reversal of the electromagnet 740, will release internal magnets 710, and with the help of an large coil spring 724 disposed inside the ratcheting system, the needle support plate 726a,b is returned to the bottom, with the needles inside the vascular port 700. Medical personnel can then press the center button 722 to cause the teeth 718 of the top ratchet portion 714 to engage with the teeth 716 of the bottom ratchet portion 712 forcing the bottom ratchet portion 712 to rotate one notch at a time for each use of the vascular access port 700, displacing with it the needle support plate 708 and thus positioning the needles 726a,b at a new location as described in relation to FIGS. 8a to 8d below. The medical personnel have the option of repeatedly depressing button 722 in order to further advance the needles to other positions.

The details of the ratcheting mechanism are described in FIG. 7d. The vascular access port 700 may include a button 722 at the center of cover 702. The button 722 is attached to a central rod 732 and propped in the upward position by an inner coil spring 744. When the button 722 is depressed, the central rod 732 shifts down and pushes an shutter 734 that slides through an opening 738 in the base 702 and collapse the wall of the catheter bridges 736a,b (only one shown)

connecting both catheter 728*a,b*. Rod 732 is separate from shutter 734 to allow the button 722 to have a larger range of motion than required for shutter 734, easing use by the medial personnel. The purpose and operation of this system is reviewed in greater details with regard to FIGS. 9*a* to 9*d* below.

FIGS. 8*a* to 8*d* illustrate various stages of the operation of the ratcheting system shown in FIG. 8*a* of vascular access port 700. In the first stage, shown in FIG. 8*b*, the top portion 714 and bottom portion 712 of the ratcheting system are disposed around a large coil spring 724. Dots 742*a* to 742*e* illustrate the rotation of the bottom portion 712 in relation to the top portion 714 upon a downward motion of the needles 726*a,b* after an initial use of the vascular access port 700, FIGS. 8*b* and 8*c*, then how the bottom teeth 716 engage in an adjacent groove 720 between top teeth 718, shown in FIG. 8*d*. The ratcheting action forces the teeth 718 to move the next position for engagement with the teeth 716, and the coil spring 724 creates a torsional force as it is compressed by button 722 that will drive the top portion 714 rotationally.

FIGS. 9*a* to 9*d* illustrate the operation of the button 722 of vascular access port 700 as shown in FIG. 7*d*. As viewed in FIGS. 9*a* and 9*b*, the needles 726*a,b* of the vascular access 700 are functioning in a blood flow mode. The button is in an upper position flush with the top surface of the cover 704, with central rod 732 being collinear with, but not engaging shutter 734. Valve 748*a* of needle 728*a* is open and against the wall of the needle 726*a*, and similarly, valve 748*b* of needle 728*b* is open and against the wall of the needle 726*b*. In this configuration the blood circulates out of needle 726*b*, and back into needle 726*a* as when the vascular access port is used for hemodialysis of a patient with kidney failure.

As viewed in FIGS. 9*c* and 9*d*, the needles 726*a,b* of the vascular access 700 are functioning in a cleaning mode. The button 722 is in a depressed position. In this configuration the blood circulates in catheter 728*a* and 728*b* through lower bridge catheter 746*b* and a cleaning solution may be circulated in needles 726*a* and 726*b* through upper bridge catheter 746*a*. Valve 748*a* of needle 726*a* is closed and blocking the flow between the needle 726*a* and catheter 728*a*, and similarly, valve 748*b* of needle 726*b* is closed and blocking the flow between the needle 726*b* and catheter 728*b*.

Valves 748*a* and 748*b* for connection to catheters 728*a* and 728*b* respectively may be of any sliding or rotational design incorporated into the body of the vascular access port 700 following well known engineering principles to provide the fluid controls described in FIG. 9*b* and FIG. 9*d*.

Figure 10A:
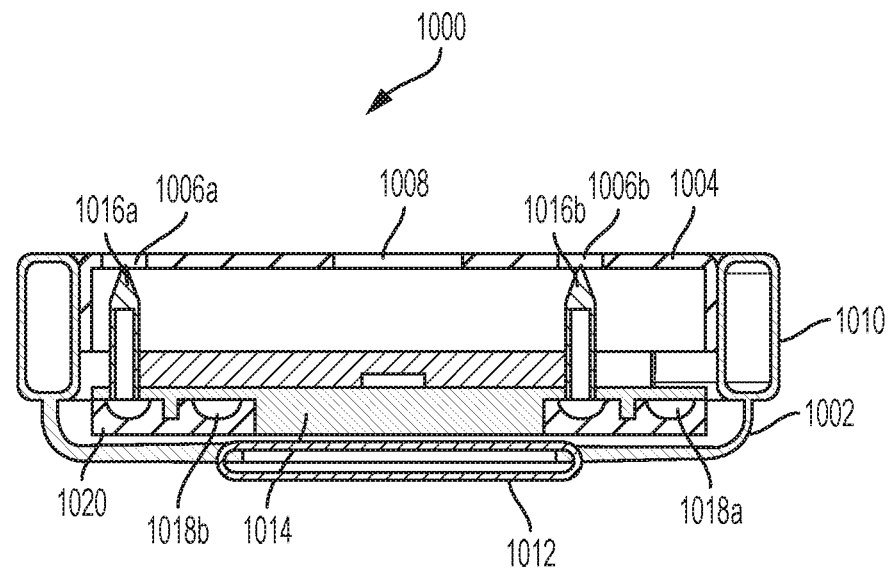
FIG. 10a illustrates a cross-sectional view of an example of a vascular access port contemplated herein, with the needles in the retracted position.
Figure 10B:
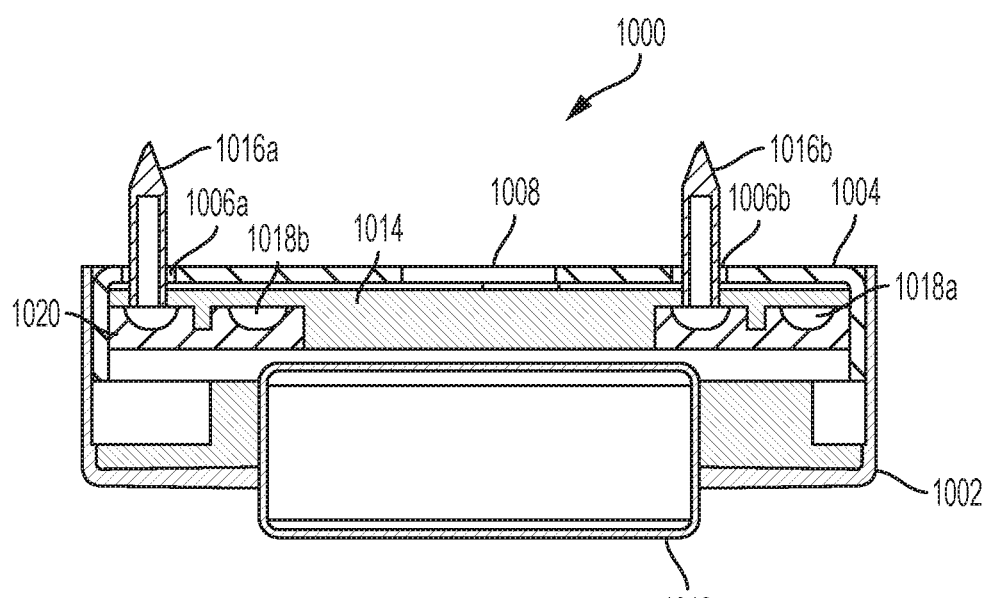
FIG. 10b illustrates a cross-sectional view of the vascular access port of FIG. 10a, with the needles in the extended position.

FIGS. 10*a* and 10*b*, illustrate another example of a vascular access port 1000 with an alternate elevator mechanism. The access port 1000 may generally include a lower body 1002 supporting a cover 1004. The cover 1004 may have on the top surface a series of openings 1006*a,b* to allow the passage of needles 1016*a,b* respectively, through the top in and out of the vascular access port 1000. The vascular access port 1000 may also be contained in a housing that prevents access of body fluids or ingrowth of body tissue into the port. The housing may be made of a self-healing material, such as silicone. Alternatively, the cover 1004 may be made of a self-healing material, and the needles 1016*a,b* pierce through the cover 1004. The openings created in the self-healing material closes upon retraction of the needles so that the vascular access port 1000 remains impervious to body fluids and ingrowth of body tissue. Inside the vascular access port 1000, the needles 1016*a,b* may be supported by a support plate 1014. The needle support plate 1014 contains circular channels 1018*a,b* in fluid communication with the lumen of needles 1016*a,b*, respectively, at the bottom surface of the needle support plate 1014, and to the lumen of the catheters that access the blood vessels of a patient (not shown). The circular channels may be defined by the bottom wall of the needle support plate 1014 in the form of two grooves in the bottom surface in which are fitted a circular ring 1020 having also two circular grooves, hence defining channels 1018*a,b*.

In operation, the elevator mechanism of the vascular access port 1000 may be activated to raise the needles 1016*a,b* by medical personnel squeezing the sides of the vascular access port 1000, on the side balloons 1010 (as shown in FIG. 10*a*) shifting air or gas or a fluid contained therein to a bottom balloon 1012 (as shown in FIG. 10*b*). Inflation of balloon 1012 raises needle plate 1014, forcing needles 1016*a,b* though openings 1006*a,b*. An opening 1008 at the center of the cover 1004, may be used to place a ratcheting mechanism to move the axial position of the needles inside the vascular access port 1000, as well as a valve activating system to allow cleaning of the needle as previously described above.

Figure 11:
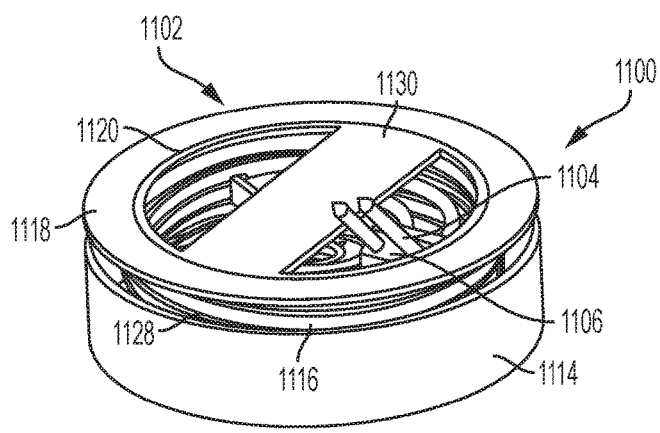
FIG. 11 illustrates a perspective view of an example of a vascular access port contemplated herein, with the needles in the extended position.
Figures 12, 13:
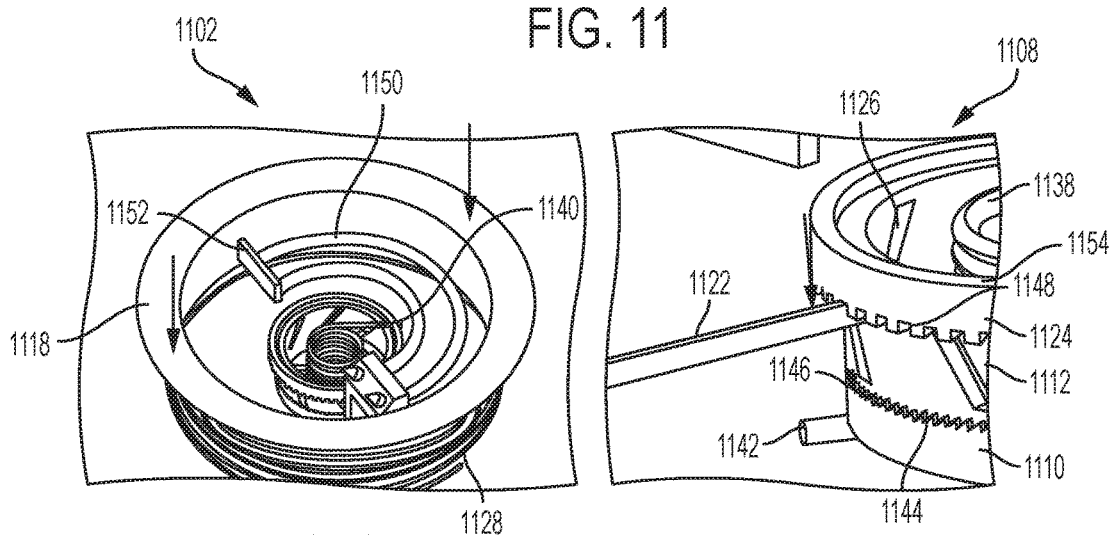
FIG. 12 illustrates a perspective view of the ratcheting mechanism as shown in FIG. 11, with the needles in the retracted position.
FIG. 13 illustrates a perspective view of a portion of the ratcheting mechanism as shown in FIG. 12, with the needle in the retracted position.

FIGS. 11 to 13 illustrate another example of a vascular access port 1100 with an elevator mechanism and needle shifting mechanism. In this example, the cover has been removed to expose the elevator and needle-shifting mechanisms 1102. A cupped body 1114 contains a cylinder 1116, which has, at the top, a flange 1118 and is supported by a coil spring 1128 disposed between the cylinder 1116 and the cupped body 1114. A ratcheting system 1108 may include a button 1120 disposed in the cylinder 1116. The button 1120 may include a bridge 1130 that spans the diameter of the button 1120. Inside the vascular access port 1100, the needles 1104 may be supported by an arm 1106 that is connected to a bottom ratchet portion 1110 of a ratcheting system 1108. Referring to FIG. 12, the needle arm 1106 may contain channels connected to the needle shafts at one end and to the vascular catheters (not shown) at catheter inlets (not shown) at the other end. The needles may also include shafts 1150 supported by another arm 1152.

Referring to FIG. 13, the ratcheting system 1108 is circular and disposed inside the cupped body 1114. The ratcheting system 1108 may also include a top ratchet portion 1112 disposed above a bottom ratchet portion 1110. The top ratchet portion 1112 may have a cylindrical wall with a series of slits 1126 for receiving a bar 1122 which connects a cylinder 1116 to circular outer ratchet 1124 of the ratcheting system 1108. The ratcheting system 1108 may include a torsion spring 1138, with a top end 1140 engaged in the top rim 1154 of the outer ratchet 1124, and the bottom end 1142 engaged with the bottom ratchet portion 1110.

Referring to FIGS. 12 and 13, when the flange 1118 is depressed by the medical personnel, it triggers the elevator mechanism of the ratcheting system 1108 to shift the position of the needles 1104 up through the arm 1106. The ratcheting system 1108 shifts the arm 1106 clockwise forcing the needle shafts 1136 to slide through the channels in the arm 1106. Because the channels are oblique, the needles are elevated. When the button 1120 is depressed, it activates the needle-shifting mechanism such that the bar 1122 slides in one of the slits 1126, rotating clockwise the top ratchet portion 1112 as the bar 1122 shifts downward disengaging the outer ratchet 1148. The teeth 1146 of the top ratchet portion 1112 engage with the teeth 1144 of the bottom ratchet portion 1110 forcing both top ratchet portion 1112 and bottom ratchet portion 1110 to rotate together, displacing the needles 1104 out of the arm 1106. Outer ratchet 1148 serves to prevent the coil spring 1138 from releasing until sufficient energy is stored in the coil spring 334 to drive the needles upward.

Figures 14A, 14B:
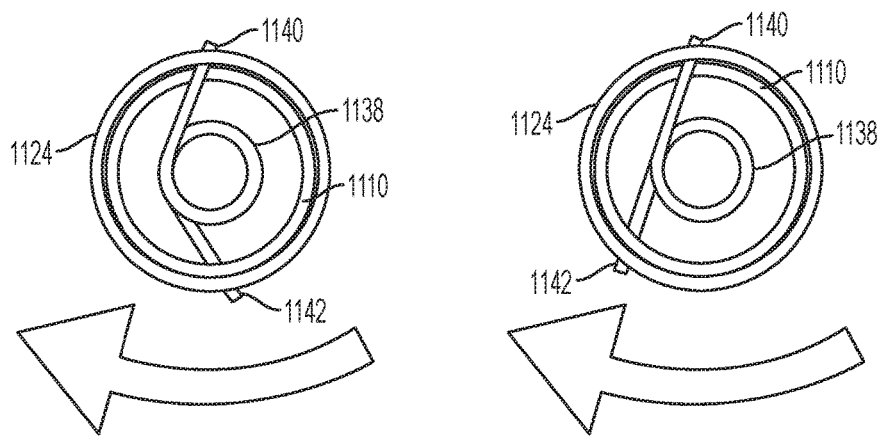
FIGS. 14a and 14b illustrate top views of the configurations of a torsion spring used in the ratcheting mechanism as shown in FIG. 12.
Figure 15:
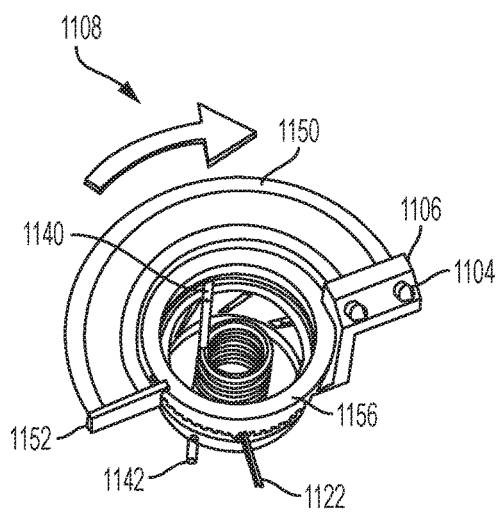
FIG. 15 illustrates a perspective view of the ratcheting mechanism as shown in FIG. 12, with the needles in the retracted position.

FIGS. 14a and 14b illustrate top views of the configurations of a torsion spring used in the ratcheting mechanism as shown in FIG. 12. When button 1120 is depressed, a clockwise rotational force of both the top ratchet portion 1112 and bottom ratchet portion 1110, together, is applied to the bottom end 1142 of the torsion spring 1138. When button 1120 is depressed a sufficient number of times, the ratcheting mechanism will release the coil spring 1138 to drive the needles upward. FIGS. 14a to FIG. 18c illustrate this process. When button 1120 is depressed bottom ratchet portion 1110 is rotated clockwise relative to outer ratchet 1124, which includes one end 1140 of torsion spring 1138 causing energy to be stored in torsion spring 1138. Referring to FIG. 15, the needle shaft supporting arm 1152 is connected to an uppermost ring 1156 which provides access for cannula connections (not shown). Needles shafts 1150 schematically illustrate that a connection is to be provided between the supporting arm 1156 and needles 1102. Needle shafts 1150 may be made of a suitable flexible or extendable material to allow the movement of needle to occur.

Figure 16:
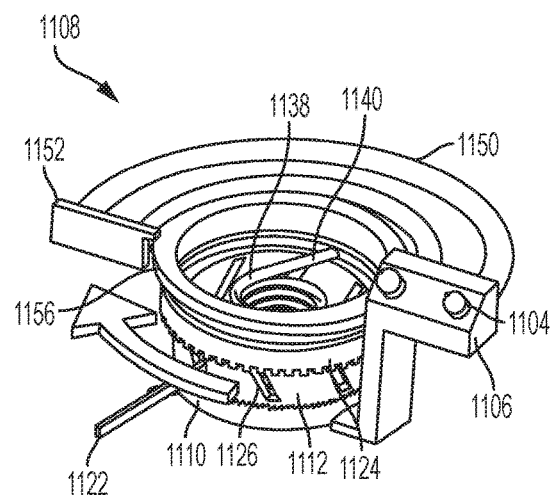
FIG. 16 illustrates a perspective view of the ratcheting mechanism as shown in FIG. 12, with the needles in the retracted position.

FIG. 16 illustrates a partial perspective view of the ratcheting mechanism as shown in FIG. 12, with the needle in the retracted position. Outer ratchet 1124 rotates clockwise relative to top ratchet portion 1112 as button 1120 is depressed causing the ratcheting mechanism to be driven.

Figure 17A:
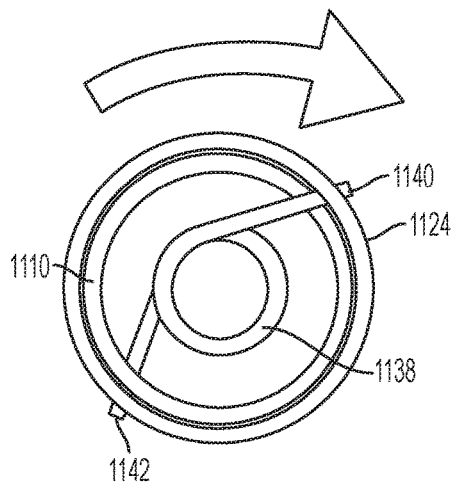
FIGS. 17a and 17b illustrate top views of the various configurations of a torsion spring used in the ratcheting mechanism as shown in FIG. 12.
Figure 17B:
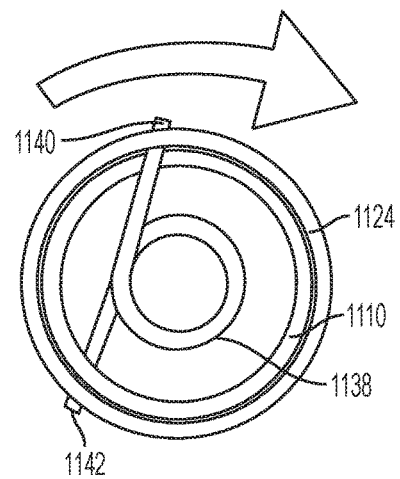
Figure 18A:
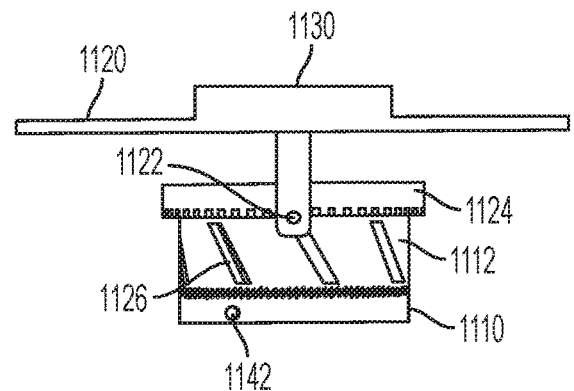
FIGS. 18a to 18c illustrate side views of the various configurations of the ratcheting mechanism as shown in FIG. 12.
Figure 18B:
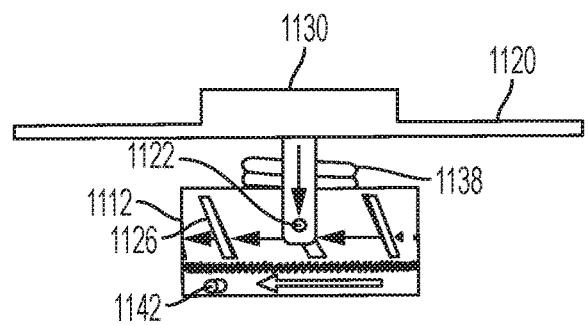
Figure 18C:
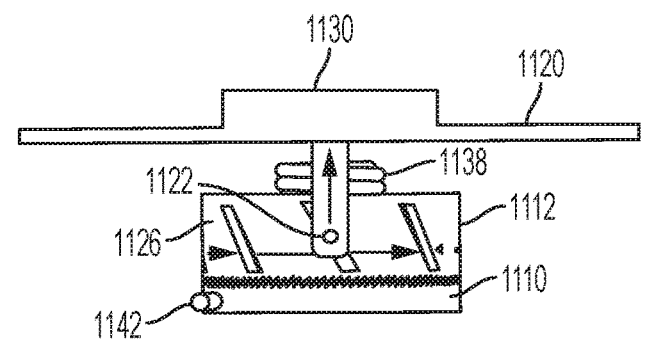

FIGS. 17a and 17b illustrate top views of the configurations of a torsion spring used in the ratcheting mechanism as shown in FIG. 12 when a clockwise rotation force by the outer ratchet 1124 is applied to the top end 1140 of the torsion spring 1138. When the torsion spring 1138 is sufficiently energized the ratcheting mechanism has rotated such that locking bar 1122 is released. The needles 1102 are driven forward by the movement of the torsion spring end 1140 relative to the other end of the torsion spring 1142, causing the needles to move out of the vascular port body. FIGS. 18a to 18c illustrate side views of the configurations of the ratcheting mechanism as shown in FIG. 12.

Figure 19:
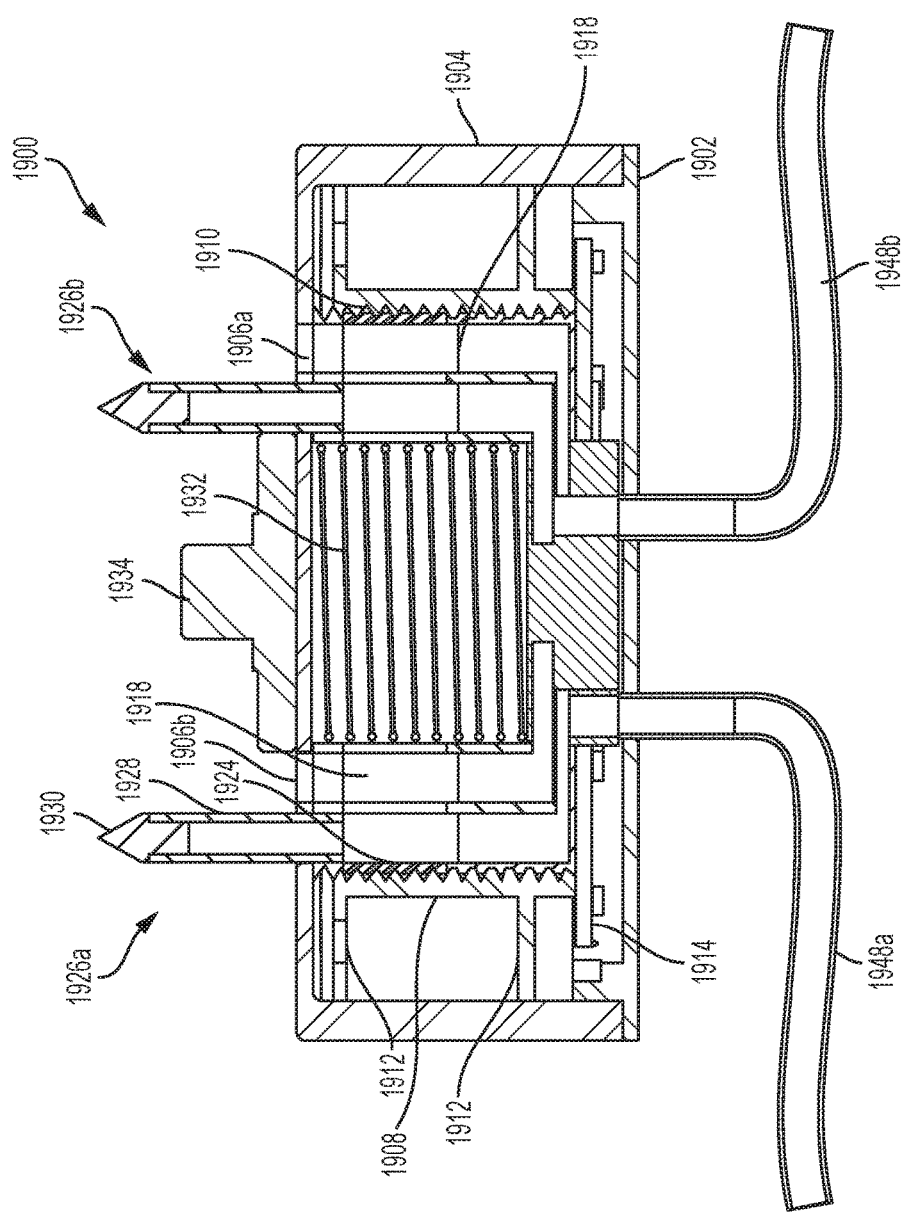
FIG. 19 illustrates a cross-sectional view of an example of a vascular access port contemplated herein, with the needles in extended position, and flow path open.
Figure 20:
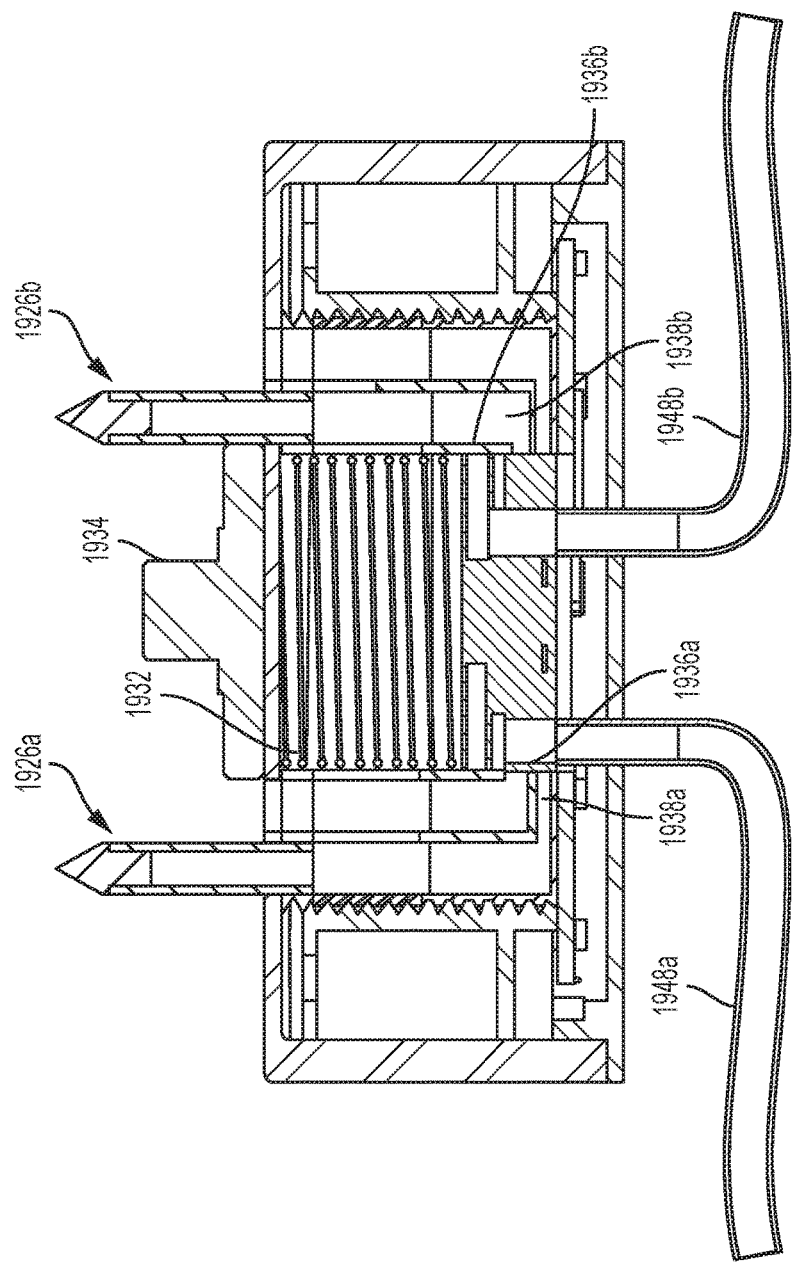
FIG. 20 illustrates a cross-sectional view of the vascular access port of FIG. 19, with the needles in extended position, and flow path closed.

FIGS. 19 and 20 illustrate the operation of a vascular access port 1900 to open or close flow of fluid through the vascular access port 1900. FIG. 19 illustrates the access port 1900 in an open configuration where fluid or blood can flow from the opening of the needles through the port and into the body catheters. The vascular access port 1900 may generally include a base plate 1902 supporting a cover 1904. The cover 1904 may have on the top surface a series of openings 1906a,b to allow the passage of needles 1926a,b through the top in and out of the port. The vascular access port 1900 may be contained in a housing that prevents access of body fluids or ingrowth of body tissue into the port. The housing may be made of a self-healing material of the cover or housing, such as silicone. Alternatively, the cover 1904 may be made of a self-healing material, and the needles 1926a,b pierce through the cover 1904. The openings created in the self-healing material closes upon retraction of the needles so that the vascular access port 1900 remains impervious to body fluids and ingrowth of body tissue. The base plate 1902 also supports a floor plate 1914 onto which rests a cylinder 1908. The cylinder 1908 may include threads 1910 in the interior, and on the periphery, flanges 1912 to receive permanent magnets (not shown).

The needles 1926a,b are supported within the interior of the cylinder 1908 by a needle holder 1918. The needle holder 1918 may have threads 1924 on the periphery that engages the threads 1910 of the cylinder 1908. Each needle 1926 may include a shaft 1928 for connecting through a fluid path with internal catheters 1948a,b accessing the blood vessel, and removable a tip 1930 which allows access to the lumen of the needles 1926a,b for the passage of fluids or blood.

FIG. 20 illustrates the vascular port 1900 in a close configuration where fluid or blood cannot flow through the vascular access port 1900. At the center of the vascular access port 1900, a valve mechanism may be used by the medical personnel to open or close the flow of fluid through the vascular access port 1900. A coil spring 1932 may be compressed by depressing button 1934, sliding valves 1936a,b to close channels 1938a,b.

The needles contemplated herein, may include any hollow cylinder or shaft. The needle may include, in some examples, standard bevels, short bevels, true short bevels, etc. Furthermore, the needles may exhibit an outer diameter in the range of 0.1 mm to 4.6 mm, including all values and increments therein. In addition, the needle may exhibit an inner diameter in the range of 0.08 mm to 4.0 mm, including all values and increments therein. Furthermore, the needles may exhibit a nominal wall thickness in the range of 0.002 mm to 0.4 mm including all values and increments therein. The needles may be formed of stainless steel, ceramic composites, or other materials. In addition, the needles or the needle tips may be replaceable in case of dulling.

Accordingly, a method of injecting a composition into a subject may be provided using the access port described herein. Once the port with at least one needle has been implanted in the patient and at least one internal catheter has been inserted into a vascular vein or body channel of a patient in need of the repeated systemic or local therapy, the access port may be accessed and therapy delivered according to the following steps. Medical personnel apply an activator over the access port and activate the elevator mechanism in the direction that will raise the at least one needle out through the cover of the access port, piercing the skin at a first location. The activator is put aside. The at least one needle is then connected to an syringe, or bag containing the composition through appropriate tubing or catheter. The composition is injected as a bolus or drip, or infused at the prescribed rate. Once the therapy has been delivered, the activator is placed again over the access port and activated in a reversed direction that lowers the at least one needle under the skin and into the access port, under the cover. The activator is maintained until the activator engages the needle shifting mechanism to displace the at least one needle from the position just used to a new position inside the access port such that when the access port is accessed again at the next therapy session, the needle will protrude at a new location.

A composition may include pharmaceuticals, nutrients, contrasting agents, blood or blood components, such as plasma, platelets, white blood cells, red blood cells, etc. Furthermore, a patient may include any vertebrate or invertebrate, including humans, other mammals, apes, domestic animals, cattle, etc. A vascular access port may be implanted into the patient and the catheter may be inserted into a vein. The needle may be extended from the port upon actuation and may puncture the skin. A composition may be introduced to the subject by either injecting the composition into the needle or otherwise introducing the needle into a container, such as through a vial stopper. Once administration of the composition is finished, the needle may be retracted or otherwise positioned back through the skin and into the port.

Alternatively, vascular access ports as described herein are suitable for use in hemodialysis of patient in need thereof, including patients in renal kidney failure and end stage renal disease. Once the vascular access port with at least two needles has been implanted in the patient and at least two internal catheters have been inserted into a vascular vein of a patient in need of the repeated hemodialysis, the port may be access and therapy performed according to the following steps. A medical personnel, apply an activator over the vascular access port and activate the elevator mechanism in the direction that will raise the at least two needles out through the cover of the vascular access port, piercing the skin at a first location. The activator is put aside. The at least two needles are then connected to a hemodialysis machine through appropriate tubing or catheters, one to receive the blood to be purified or filtered, the other to return the clean blood to the patient. Once the therapy has been delivered, the activator is placed again over the vascular access port and activated in a reversed direction that lowers the at least two needles under the skin and into the vascular access port, under the cover. The activator is maintained until the activator engages the needle shifting mechanism to displace the at least two needles from the position just used to a new position inside the vascular access port such that when the vascular access port is accessed again at the next therapy session, the needles will protrude at a new location.

The vascular access port described herein may be modified to define one of the possible axial positions of the needles to perform routine maintenance of the vascular access port. For example, the needles may be made of a conductive material, and when occupying the maintenance position, become connected to wiring that feeds a battery or a microprocessor in the vascular access port. The needles can then be connected to a power supply to recharge the vascular access port battery, to a computer for data transfer from a microprocessor in the vascular access port, or to control inputs for the operation of the vascular access port by a microprocessor.

The battery may be useful in a vascular access port that operates the needles extraction/retraction as well as rotation through a motor. Also, the battery may power a drug dispensing pump or other such mechanism that provides a release of a composition to the patient. Batteries may also be used to power implantable sensors or devices to transmit or receive information that provide diagnostic information to a clinician or still further another implantable device. Such information provided may include operational information on the vascular port, such as the position of needles in the port, the number of uses the port has experienced, the time between uses, etc. A vascular port may include a microprocessor so as to provide storage and processing of such information, programmable control of flow through the port or other such operations, means of preventing inadvertent operation of the port by requiring recognition of security passwords or for other means that my provide useful interaction with the port, external devices or with the clinician, however indirectly.

Alternatively, the needles may include removable and replaceable tips that allow electrical connection inside the needle body. Such tips may be reused after appropriate cleaning or preferably exchanged for sterilized replacements. Electrical connections may be made directly with the tips or via a mechanism exposed after tips are removed.

One or more maintenance positions may be used also to deliver chemicals to resupply a reservoir in the vascular access port that time-releases medicine to the patient, or that feeds a chemical battery, such as a fuel cell. The needles can then be connected to a separate channel that leads to the reservoir, or battery. In some embodiments, the chemical may be a gas for use in establishing pressure, such as to operate a pump that time-releases drug to the patient.

Alternatively, a maintenance position may be used to deliver a device to the vascular access port, such as replacement of a battery, vascular access port parts, RFID chips, microprocessors, encapsulated drugs, and the like.

To perform a maintenance operation, medical personnel, apply an activator over the vascular access port and activate the port in the direction which will engage the needle shifting mechanism to position the at least one needle at the maintenance location. Then, the activator is then set to engage the elevator mechanism to raise the at least one needle out through the cover of the vascular access port, piercing the skin at the maintenance location. The activator is put aside. The at least one needle is then used to performed the required maintenance as described above. Once the maintenance operation has been performed, the activator is placed again over the access port and activated in a reversed direction that lowers the at least one needle under the skin and into the access port, under the cover. The activator is maintained to operate the activator to engage the needle shifting mechanism to displace the at least one needle from the position just used to a new position inside the port such that when the vascular access port is accessed again at a therapy session, the needle will protrude at a location designated for performing the required therapy.

The foregoing description of several methods and embodiments has been presented for purposes of illustration. It is not intended to be exhaustive or to limit the claims to the precise steps and/or forms disclosed, and obviously many modifications and variations are possible in light of the above teaching. For example, other elevator mechanisms have been previously described in U.S. Pat. No. 8,377,034 which is incorporated herein by reference in its entirety. Such elevator mechanism may be used in the vascular access port described herein interchangeably. It is intended that the scope of the invention be defined by the claims appended hereto.

What is claimed is:

1. A medical device comprising:
   an implantable access port having an access port body and at least one needle;
   the at least one needle housed within the access port body, the at least one needle extendable and retractable relative to the access port body;
   a needle shift mechanism housed within the access port body, the needle shift mechanism movable within the access port body to move the at least one needle to a plurality of different positions of the access port body at which the at least one needle is extendable and retractable;
   wherein the needle shift mechanism is rotatable around an axis; and the at least one needle is extendable and retractable axially along the axis;
   wherein the at least one needle comprises a needle shaft with a needle lumen, and a removable needle tip which is configured to be connectable to and removable from the needle shaft; and
   wherein the needle lumen is closed by the removable needle tip when the removable needle tip is connected to the needle shaft.

2. The device of claim 1 wherein:
   the removable needle tip is replaceable on the needle shaft after being removed from the needle shaft.

3. The device of claim 1 wherein:
   the removable needle tip is a pointed needle tip.

4. The device of claim 1 wherein:
the removable needle tip is mechanically connectable to the needle shaft.

5. The device of claim 4 wherein:
the needle shaft is configured to connect with a plurality of replaceable needle tips.

6. The device of claim 1 wherein:
the needle shift mechanism is movable such that the at least one needle is rotatable along an arcuate path about an axis of rotation.

7. The device of claim 6 wherein:
the arcuate path is defined by a substantially constant radius from the axis of rotation.

8. The device of claim 6 wherein:
the plurality of different positions of the access port body are arranged along the arcuate path.

9. The device of claim 6 wherein:
the plurality of different positions are substantially equally spaced along the arcuate path.

10. The device of claim 6 wherein:
the at least one needle is rotatable along the arcuate path about the axis of rotation in only one direction.

11. The device of claim 1 wherein:
the needle shift mechanism comprises a ratcheting mechanism.

12. The device of claim 1 wherein:
the access port body comprises a cover; and
the at least one needle is extendable and retractable through the cover.

13. The device of claim 1 wherein:
the access port body comprises a septum; and
the at least one needle is extendable and retractable through the septum, whereby an opening in the septum through which the at least one needle extends closes after the at least one needle is retracted from the septum.

14. The device of claim 1 wherein:
the access port body comprises a plurality of needle openings; and
the at least one needle is extendable and retractable through each of the plurality of needle openings.

15. The device of claim 14 wherein:
the plurality of needle openings comprise a first needle opening and a second needle opening;
the plurality of different positions comprise a first position and a second position; and
the needle shift mechanism is movable within the access port body to move the at least one needle from the first position in which the at least one needle is aligned with the first needle opening to extend and retract through the first needle opening to the second position in which the at least one needle is aligned with the second needle opening to extend and retract through the second needle opening.

16. The device of claim 1 wherein:
the at least one needle further comprises a first needle and a second needle; and
the needle shift mechanism is movable within the access port body to move the first needle to a plurality of different first needle positions of the access port body at which the first needle is extendable and retractable, and the second needle to a plurality of different second needle positions of the access port body at which the second needle is extendable and retractable.

17. The device of claim 16 wherein:
the needle shift mechanism is movable such that the first needle and the second needle are rotatable along an arcuate path about an axis of rotation.

18. The device of claim 1 further comprising:
a needle elevator mechanism movable within the access port body to extend the at least one needle from the access port body and retract the at least one needle into the access port body.

19. The device of claim 18 wherein:
the access port body comprises a cover having at least one opening; and
the needle elevator mechanism is movable within the access port body to extend the at least one needle from the access port body through the at least one opening in the cover and retract the at least one needle into the access port body through the at least one opening in the cover.

20. The device of claim 18 wherein:
the needle elevator mechanism is movable to extend the at least one needle from the access port body and retract the at least one needle into the access port body by rotating the needle elevator mechanism about an axis of rotation.

21. The device of claim 18 further comprising:
an external actuator; and
wherein the needle elevator mechanism is movable with the external actuator.

* * * * *